(12) United States Patent
Ji et al.

(10) Patent No.: US 8,442,835 B2
(45) Date of Patent: May 14, 2013

(54) METHODS, SYSTEMS, AND PRODUCTS FOR MEASURING HEALTH

(75) Inventors: Lusheng Ji, Randolph, NJ (US); Hisao Chang, Cedar Park, TX (US); Robert R. Miller, II, Convent Station, NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 394 days.

(21) Appl. No.: 12/817,255

(22) Filed: Jun. 17, 2010

(65) Prior Publication Data

US 2011/0313774 A1   Dec. 22, 2011

(51) Int. Cl.
*G10L 21/00* (2006.01)

(52) U.S. Cl.
USPC ........... 704/272; 704/231; 704/251; 704/270; 704/271; 704/273; 704/274; 704/275; 704/1

(58) Field of Classification Search .................. 704/231, 704/251, 270–275
See application file for complete search history.

(56) References Cited

U.S. PATENT DOCUMENTS

| | | | | |
|---|---|---|---|---|
| 4,838,275 A * | 6/1989 | Lee | | 600/483 |
| 4,933,873 A * | 6/1990 | Kaufman et al. | | 704/270 |
| 5,335,313 A * | 8/1994 | Douglas | | 704/275 |
| 5,442,728 A * | 8/1995 | Kaufman et al. | | 704/270 |
| 5,577,164 A * | 11/1996 | Kaneko et al. | | 704/275 |
| 6,014,626 A * | 1/2000 | Cohen | | 704/275 |
| 6,256,019 B1 * | 7/2001 | Allport | | 345/169 |
| 6,411,933 B1 * | 6/2002 | Maes et al. | | 704/273 |
| 6,535,131 B1 * | 3/2003 | Bar-Shalom et al. | | 340/573.1 |
| 6,646,541 B1 * | 11/2003 | Wang et al. | | 340/3.54 |
| 6,885,736 B2 * | 4/2005 | Uppaluru | | 379/88.17 |
| 6,906,696 B2 * | 6/2005 | Allport | | 345/156 |
| 6,911,916 B1 * | 6/2005 | Wang et al. | | 340/3.7 |
| 6,968,223 B2 * | 11/2005 | Hanover | | 600/407 |
| 7,143,044 B2 * | 11/2006 | Zadrozny et al. | | 704/275 |
| 7,155,371 B2 * | 12/2006 | Kawatahara et al. | | 702/187 |
| 7,310,668 B2 * | 12/2007 | Brown | | 709/224 |
| 7,399,276 B1 * | 7/2008 | Brown et al. | | 600/300 |
| 7,541,547 B2 * | 6/2009 | McGuire et al. | | 177/25.13 |
| 7,555,425 B2 * | 6/2009 | Oon | | 704/9 |
| 7,657,444 B2 * | 2/2010 | Yu | | 705/3 |
| 7,778,852 B2 * | 8/2010 | Vasko et al. | | 705/3 |
| 7,925,508 B1 * | 4/2011 | Michaelis | | 704/270 |
| 8,106,752 B2 * | 1/2012 | Golden | | 340/426.11 |
| 8,130,095 B2 * | 3/2012 | Allen et al. | | 340/539.12 |
| 8,140,340 B2 * | 3/2012 | Bhogal et al. | | 704/273 |
| 2003/0163299 A1 * | 8/2003 | Iliff | | 704/1 |
| 2004/0186747 A1 * | 9/2004 | Nakano et al. | | 705/3 |
| 2004/0204635 A1 * | 10/2004 | Scharf et al. | | 600/323 |
| 2005/0010416 A1 * | 1/2005 | Anderson et al. | | 704/271 |
| 2005/0101841 A9 * | 5/2005 | Kaylor et al. | | 600/300 |
| 2005/0247494 A1 * | 11/2005 | Montagnino | | 177/60 |
| 2006/0015016 A1 * | 1/2006 | Thornton | | 600/300 |
| 2006/0149558 A1 * | 7/2006 | Kahn et al. | | 704/278 |

(Continued)

*Primary Examiner* — Pierre-Louis Desir
*Assistant Examiner* — Fariba Sirjani
(74) *Attorney, Agent, or Firm* — Scott P. Zimmerman, PLLC

(57) ABSTRACT

Methods, systems, and products measure health data related to a user. A spoken phrase is received and time-stamped. The user is identified from the spoken phrase. A window of time is determined from a semantic content of the spoken phrase. A sensor measurement is received and time-stamped. A difference in time between the time-stamped spoken phrase and the time-stamped sensor measurement is determined and compared to the window of time. When the difference in time is within the window of time, then the sensor measurement is associated with the user.

20 Claims, 22 Drawing Sheets

U.S. PATENT DOCUMENTS

| | | | |
|---|---|---|---|
| 2006/0173684 A1* | 8/2006 | Fischer et al. | 704/254 |
| 2007/0054252 A1* | 3/2007 | Lin | 434/247 |
| 2007/0276277 A1* | 11/2007 | Booth et al. | 600/519 |
| 2008/0082338 A1* | 4/2008 | O'Neil et al. | 704/275 |
| 2008/0147439 A1* | 6/2008 | Maliszewski | 705/2 |
| 2008/0147604 A1* | 6/2008 | Bulow | 707/3 |
| 2008/0255428 A1* | 10/2008 | Sharda et al. | 600/300 |
| 2008/0269571 A1* | 10/2008 | Brown et al. | 600/300 |
| 2009/0097641 A1* | 4/2009 | Matsuzaki et al. | 380/44 |
| 2009/0178858 A1* | 7/2009 | Daniels et al. | 177/25.19 |
| 2009/0204411 A1* | 8/2009 | Morikawa et al. | 704/275 |
| 2009/0270743 A1* | 10/2009 | Dugan et al. | 600/500 |
| 2009/0282371 A1* | 11/2009 | Curl | 715/863 |
| 2009/0306983 A1* | 12/2009 | Bhandari | 704/251 |
| 2010/0026817 A1* | 2/2010 | Ryan et al. | 348/207.11 |
| 2010/0033303 A1* | 2/2010 | Dugan et al. | 340/5.82 |
| 2010/0036662 A1* | 2/2010 | Emmons | 704/235 |
| 2010/0056876 A1* | 3/2010 | Ellis et al. | 600/300 |
| 2010/0070867 A1* | 3/2010 | Lemmers | 715/735 |
| 2010/0191075 A1* | 7/2010 | Angelides | 600/301 |
| 2010/0223285 A1* | 9/2010 | Biddulph-Krentar | 707/769 |
| 2010/0286490 A1* | 11/2010 | Koverzin | 600/301 |
| 2011/0035234 A1* | 2/2011 | Roe et al. | 705/2 |
| 2011/0098544 A1* | 4/2011 | Shah et al. | 600/323 |
| 2011/0105919 A1* | 5/2011 | Naji | 600/500 |
| 2011/0119053 A1* | 5/2011 | Kuo et al. | 704/201 |
| 2011/0161076 A1* | 6/2011 | Davis et al. | 704/231 |
| 2011/0172994 A1* | 7/2011 | Lindahl et al. | 704/211 |
| 2011/0184735 A1* | 7/2011 | Flaks et al. | 704/240 |
| 2011/0190701 A1* | 8/2011 | Remde et al. | 604/131 |
| 2011/0260832 A1* | 10/2011 | Ross et al. | 340/5.84 |
| 2011/0276326 A1* | 11/2011 | Fumarolo et al. | 704/235 |
| 2011/0282671 A1* | 11/2011 | Dicks et al. | 704/270.1 |
| 2011/0301957 A1* | 12/2011 | Brown et al. | 704/272 |
| 2012/0109676 A1* | 5/2012 | Landau | 705/2 |
| 2012/0150545 A1* | 6/2012 | Simon | 704/270 |
| 2012/0219271 A1* | 8/2012 | Vunic et al. | 386/278 |
| 2012/0220276 A1* | 8/2012 | Kobylarz | 455/414.1 |
| 2012/0265535 A1* | 10/2012 | Bryant-Rich et al. | 704/270 |

* cited by examiner

METHODS, SYSTEMS, AND PRODUCTS FOR MEASURING HEALTH

COPYRIGHT NOTIFICATION

A portion of the disclosure of this patent document and its attachments contain material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

BACKGROUND

Exemplary embodiments generally relate to surgery, data processing, electrical communications, and weighing scales and, more particularly, to speech signal processing, speech control, health care management, measurement systems, voice recognition, and speaker identification and verification.

Remote monitoring of health is important. Blood pressure, glucose, weight, and other health factors may be measured from home using a medical measurement device. These health factors may then be communicated to a remote location (such as a doctor's office) for analysis and tracking A common problem, though, is user binding. Many medical measurement devices are shared between multiple users. A household weight scale, for example, may be shared by multiple members of a household. The members of the household all use the same weight scale to measure their individual weights. If a weight measurement is not bound to the correct member of the household, the weight measurement may be erroneously associated with the wrong user.

BRIEF DESCRIPTION OF THE SEVERAL VIEWS OF THE DRAWINGS

The features, aspects, and advantages of the exemplary embodiments are better understood when the following Detailed Description is read with reference to the accompanying drawings, wherein.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
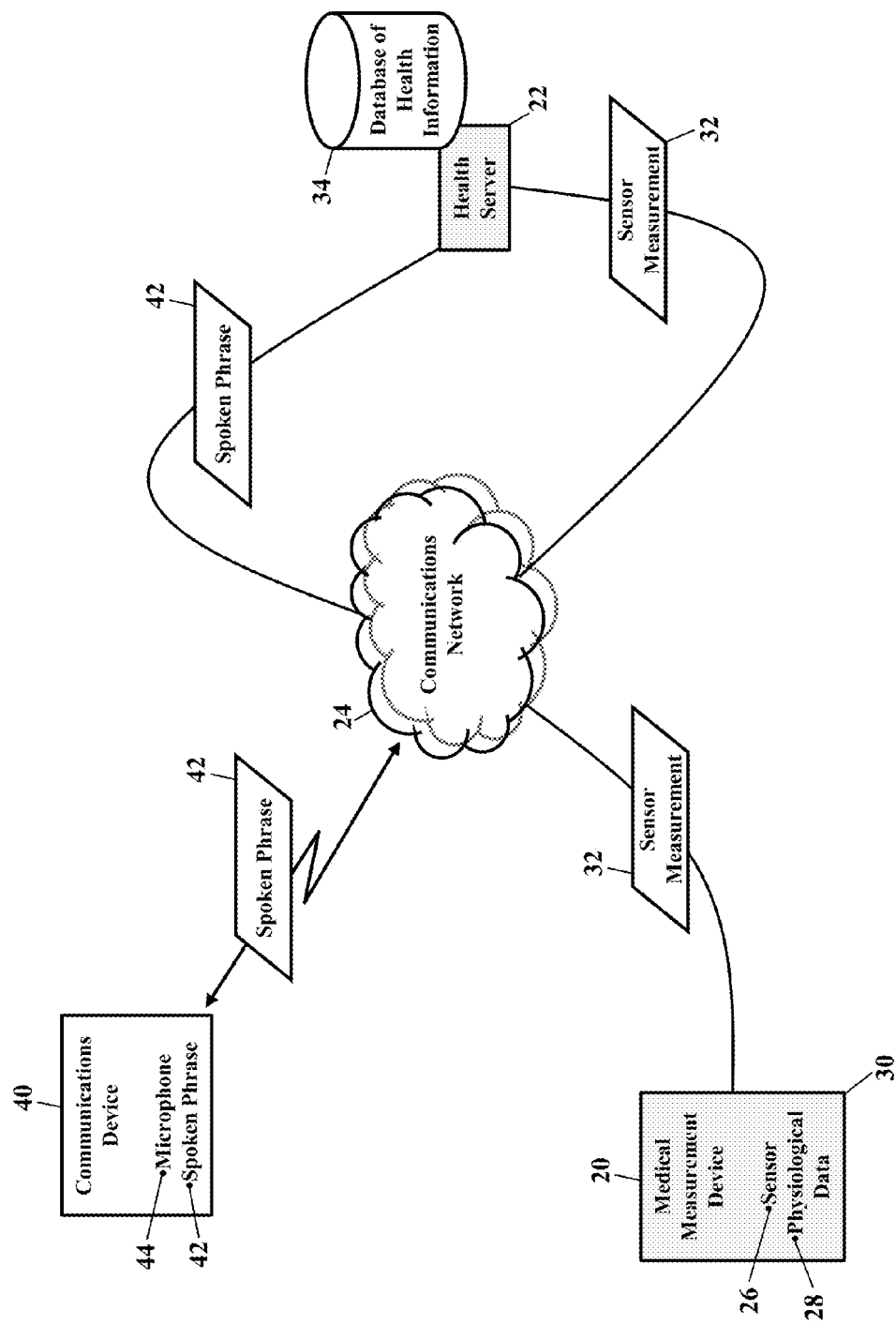
FIG. 1 is a simplified schematic illustrating an environment in which exemplary embodiments may be implemented.

FIG. 1 is a simplified schematic illustrating an environment in which exemplary embodiments may be implemented. FIG. 1 illustrates a client-server network architecture that remotely monitors a user's health factors. A medical measurement device 20 communicates with a health server 22 via a communications network 24. The medical measurement device 20 has a sensor 26 that measures any physiological data 28 related to a user's health condition. The medical measurement device 20, for example, may measure the user's weight, blood pressure, temperature, pulse rate, glucose level, height, cholesterol level, respiratory rate, or any other information or data related to the user's physiological condition. For simplicity, though, the medical measurement device 20 will be described as a bathroom weight scale 30 that measure's the user's weight. The user steps on a footpad to obtain a weight reading. When the medical measurement device 20 measures the user's weight, the medical measurement device 20 sends a sensor measurement 32 to the health server 22. The health server 22 stores the sensor measurement 32 in a database 34 of health information.

The sensor measurement 32, though, should be bound to the user. Even though the sensor measurement 32 has been received at the health server 22, the sensor measurement 32 must be associated to the correct user. Because the medical measurement device 20 is often shared among many people, the sensor measurement 32 must be correctly identified with the corresponding user. The bathroom weight scale 30, for example, is usually shared by multiple members of a household. The household members all use the same weight scale to measure their individual weights. If a weight measurement is confused with the wrong user, the health server 22 may incorrectly associate the sensor measurement 32 with the wrong user.

Exemplary embodiments, then, bind the sensor measurement 32 to the correct user. As FIG. 1 illustrates, a separate communications device 40 also communicates with the health server 22 via the communications network 24. The communications device 40 is illustrated as wirelessly communicating with the communications network 24, but the communications device 40 may be physically connected (e.g., a wireline device). As the medical measurement device 20 obtains the sensor measurement 32, the user also speaks a phrase 42 into the communications device 40. The communications device 40 may have a microphone 44 that accepts the spoken phrase 42 as an input. The communications device 40 sends an analog or digitized version of the spoken phrase 42 to an address in the communications network 24 that is associated with the health server 22. When the health server 22 receives the spoken phrase 42, the health server 22 identifies the user from the spoken phrase 42. The health server 22 then binds or associates the sensor measurement 32 to the identified user who provided the spoken phrase 42. The health server 22 may thus store the sensor measurement 32 in the database 34 of health information, and the sensor measurement 32 is associated or mapped to the correct user who provided the spoken phrase 42.

The binding is further explained using the bathroom weight scale 30. As the above paragraphs explained, the medical measurement device 20 may be the bathroom weight scale 30 that measure's the user's weight. When the user steps on the bathroom weight scale 30, the user also speaks the spoken phrase 42 into the user's communications device 40. The communications device 40 may be a cell phone, laptop, remote control, or any other processor-controlled device (as later paragraphs will explain). The communications device 40 sends the spoken phrase 42 to the health server 22, and the bathroom weight scale 30 sends the sensor measurement 32 to the health server 22. The health server 22 identifies the user from the spoken phrase 42 (as later paragraphs will explain) and associates the sensor measurement 32 to the user who provided the spoken phrase 42. Exemplary embodiments thus permit the health server 22 to accurately associate the sensor measurement 32 to the correct user who provided the spoken phrase 42. When multiple users share the bathroom weight scale 30, each user inputs the spoken phrase 42 into the communications device 40. The health server 22 identifies each user from their spoken phrase 42 and accurately associates each user's weight measurement in the database 34 of health information.

Exemplary embodiments may be applied regardless of networking environment. The communications network 24 may be a cable network operating in the radio-frequency domain and/or the Internet Protocol (IP) domain. The communications network 24, however, may also include a distributed computing network, such as the Internet (sometimes alternatively known as the "World Wide Web"), an intranet, a local-area network (LAN), and/or a wide-area network (WAN). The communications network 24 may include coaxial cables, copper wires, fiber optic lines, and/or hybrid-coaxial lines. The communications network 24 may even include wireless portions utilizing any portion of the electromagnetic spectrum and any signaling standard (such as the I.E.E.E. 802 family of standards, GSM/CDMA/TDMA or any cellular standard, and/or the ISM band). The communications network 24 may even include powerline portions, in which signals are communicated via electrical wiring. The concepts described herein may be applied to any wireless/wireline communications network, regardless of physical componentry, physical configuration, or communications standard(s).

Figure 2:
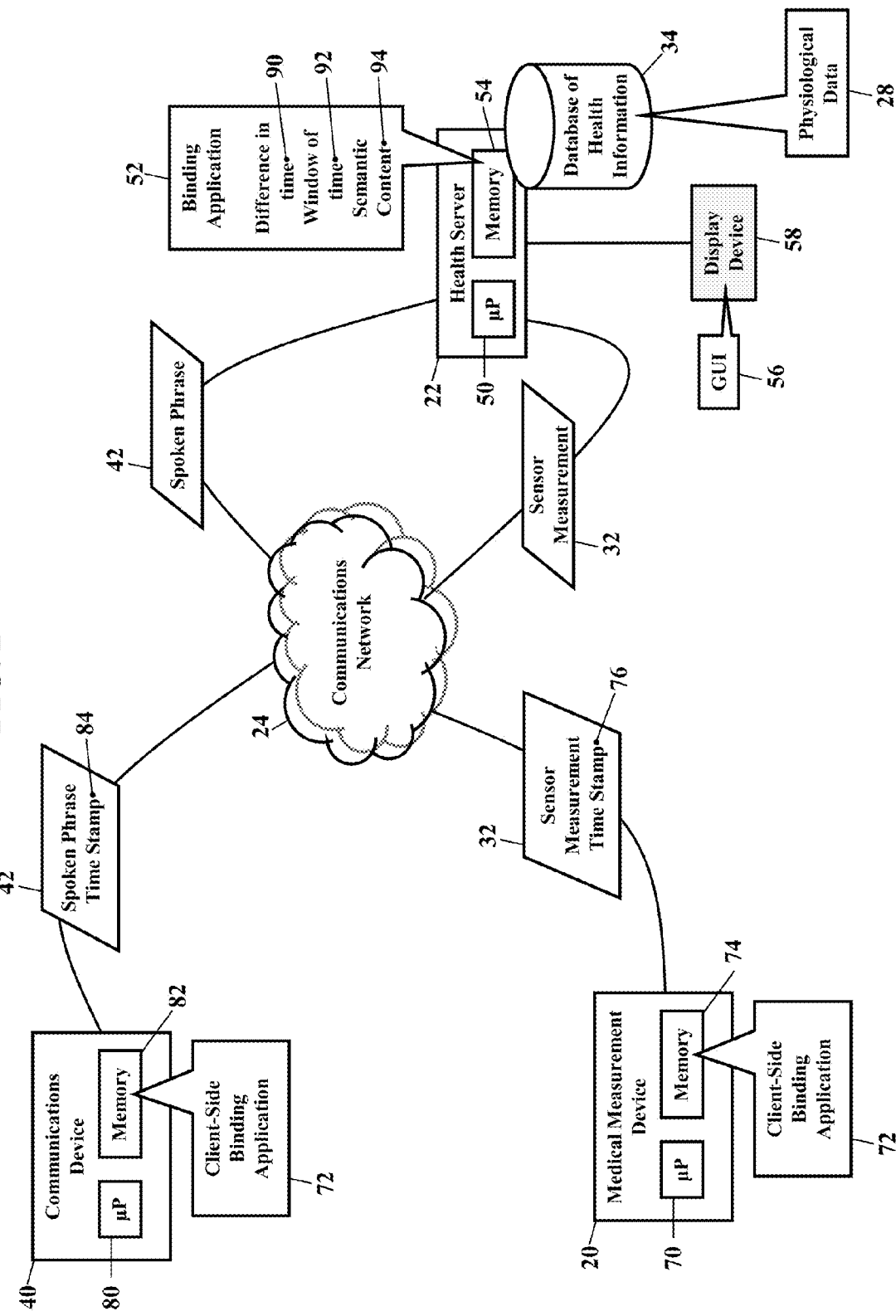
FIGS. 2 and 3 are more detailed schematics illustrating the operating environment, according to exemplary embodiments.
Figure 3:
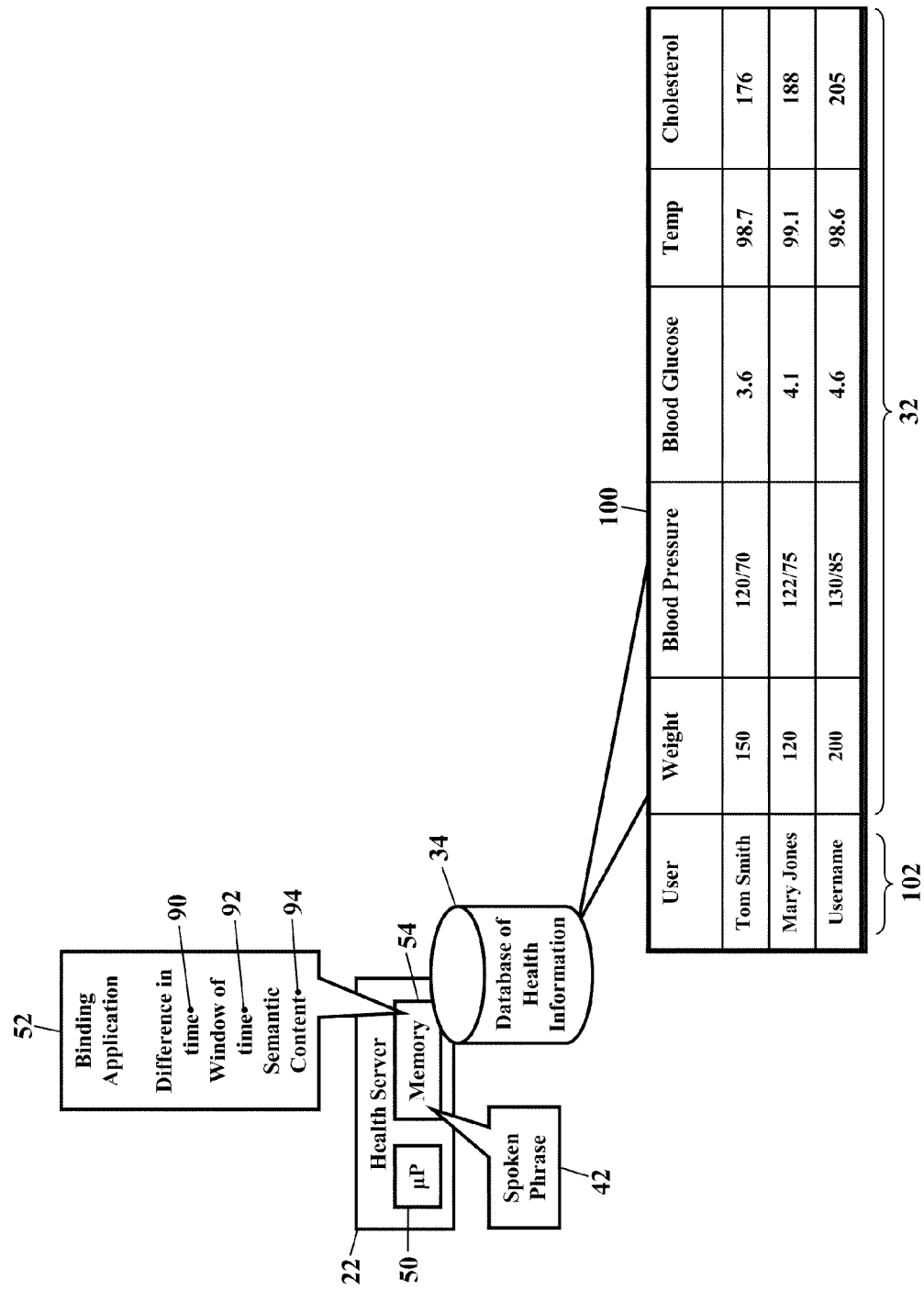
Figure 4:
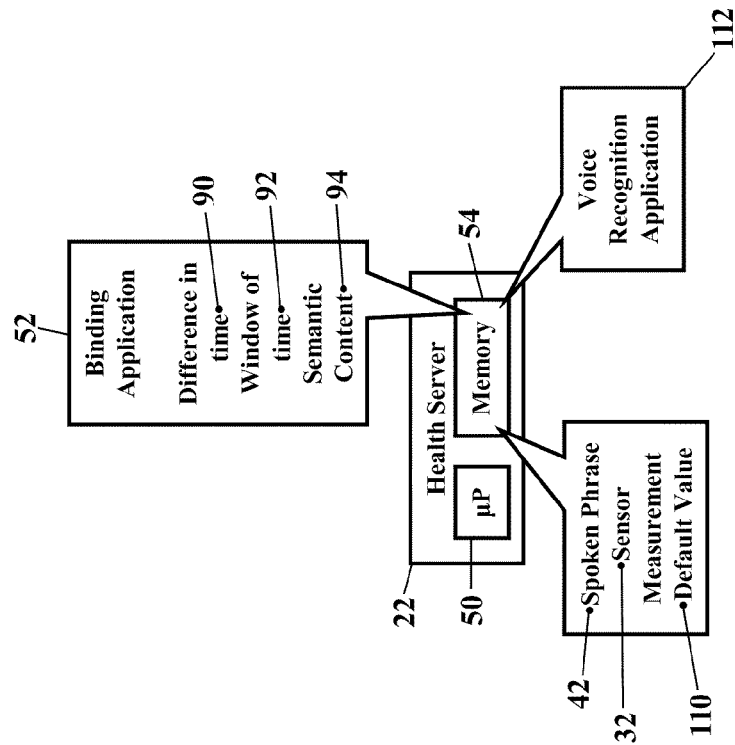
FIGS. 4-7 illustrate semantic content of a spoken phrase, according to exemplary embodiments.

FIGS. 2 and 3 are more detailed schematics illustrating the operating environment, according to exemplary embodiments. Here the health server 22 has a processor 50 (e.g., "µP"), application specific integrated circuit (ASIC), or other component that executes a binding application 52 stored in a memory 54. The binding application 52 may cause the processor 50 to produce a graphical user interface ("GUI") 56. The graphical user interface 86 is illustrated as being visually produced on a display device 58, yet the graphical user interface 56 may also have audible features. The binding application 52, however, may operate in any processor-controlled device, as later paragraphs will explain.

The health server 22 receives the sensor measurement 32 from the medical measurement device 20. The medical measurement device 20 has a processor 70 (e.g., "µP"), application specific integrated circuit (ASIC), or other component that executes a client-side binding application 72 stored in a memory 74. The client-side binding application 72 may cooperate with the binding application 52 to send the sensor measurement 32 to the address associated with the health server 22. The sensor measurement 32 may include a time stamp 76. The time stamp 76 may be added by the client-side binding application 72 and may thus represent a date/time of receipt by the medical measurement device 20. The time stamp 76, however, may be added by the binding application 52 upon receipt by the health server 22.

The health server 22 also receives the spoken phrase 42 from the user's communications device 40. The user's communications device 40 also has a processor 80 (e.g., "µP"), application specific integrated circuit (ASIC), or other component that also executes the client-side binding application 72 stored in a memory 82. The client-side binding application 72 may again cooperate with the binding application 52 to send the spoken phrase 42 to the address associated with the health server 22. The spoken phrase 42 may also include a time stamp 84. The time stamp 84 may be added by the client-side binding application 72, or the time stamp 84 may be added by the binding application 52 upon receipt at the health server 22.

The binding application 52 then correctly associates the sensor measurement 32 to the spoken phrase 42. The binding application 52 determines a difference 90 in time between the time-stamped spoken phrase 42 and the time-stamped sensor measurement 32. The binding application 52 compares the difference 90 in time to a window 92 of time. The window 92 of time is a configurable or definable parameter for binding the sensor measurement 32 to the spoken phrase 42. The window 92 of time may be retrieved from the memory 54 of the health server. The window 92 of time may also be derived from the semantic content 94 of the spoken phrase 42. When the difference 90 in time is within the window 92 of time, then the sensor measurement 32 may be confidently bound to the spoken phrase 42. The binding application 52 may thus associate the sensor measurement 32 to the user identified from the spoken phrase 42.

The window 92 of time is confidence. If the time-stamped sensor measurement 32 and the time-stamped spoken phrase 42 are contemporaneous, then the binding application 52 is assured that the sensor measurement 32 relates to the user. If the time-stamped sensor measurement 32 is stale compared to the time-stamped spoken phrase 42, then the binding application 52 may not be assured that the sensor measurement 32 relates to the user. The greater the difference 90 in time (between the time-stamped spoken phrase 42 and the time-stamped sensor measurement 32), then less relation may exist between the user and the sensor measurement 32. If the difference 90 in time lies within the window 92 of time, then the binding application 52 associates the sensor measurement 32 to the user identified from the spoken phrase 42. When, however, the difference 90 in time lies outside the window 92 of time, then the binding application 52 may consider the sensor measurement 32 to be indeterminable to any user. The binding application 52 may thus decline to associate the sensor measurement 32 with the spoken phrase 42.

The health server 22 thus builds and/or accesses the database 34 of health information. The database 34 of health information is illustrated as being locally stored in the memory 54, but the database 34 of health information may be remotely accessed and maintained at any location in communications network (illustrated as reference numeral 24 in FIG. 1). Regardless, the database 34 of health information stores the sensor measurements 32 associated with different users. FIG. 3, for example, illustrates the database 34 of health information as a table 100 that maps, relates, or otherwise associates the sensor measurements 32 to various users 102. Each sensor measurement 32 represents some physiological data (illustrated as reference numeral 28 in FIGS. 1-2) associated with a user 102. Each sensor measurement 32, for example, may indicate the user's weight, blood pressure, temperature, pulse rate, glucose level, height, cholesterol level, respiratory rate, or any other information or data related to the user's physiological condition. When the difference 90 in time (between the time-stamped spoken phrase 42 and the time-stamped sensor measurement 32) is less than or equal to the window 92 of time (in seconds or minutes, for example), then the binding application 52 associates the sensor measurement 32 to the user 102 who input the spoken phrase 42. The health server 22 thus accurately associates each user's sensor measurement 32 in the database 34 of health information.

FIGS. 4-7 illustrate the semantic content 94 of the spoken phrase 42, according to exemplary embodiments. When the health server 22 receives the spoken phrase 42 (from the user's communications device 40 illustrated in FIGS. 1-2), the binding application 52 may obtain or derive the window 92 of time from the semantic content 94 of the spoken phrase 42. If the spoken phrase 42 was "the weight scale measurement taken at 10:20 AM is Jerry's," then the binding application 52 may associate any sensor measurement 32 contemporaneous with 10:20 AM to the user "Jerry." If the window 92 of time was four minutes, for example, then the binding application 52 may bind any sensor measurement 32 having the time stamp 76 between 10:18 AM to 10:22 AM. If the spoken phrase 42 was "the weight scale measurement taken five minutes ago," then the binding application 52 may associate any sensor measurement 32 having the time-stamp 76 within the past five minutes. Because the binding application 52 may obtain the window 92 of time from the semantic content 94 of the spoken phrase 42, each individual user may flexibly specify the window 92 of time instead of relying on a default value 110 retrieved from the memory 54.

The binding application 52 may thus access or interface with a voice-recognition application 112. The voice-recognition application 112 is illustrated as being locally stored in the memory 54 of the health server 22, but the voice-recognition application 112 may be remotely accessed and called (such as via the communications network 24 illustrated in FIG. 1). The voice-recognition application 112 may receive the analog or digitized spoken phrase 42. The voice-recognition application 112 may determine the window 92 of time from the semantic content 94 of the spoken phrase 42.

Figure 5:
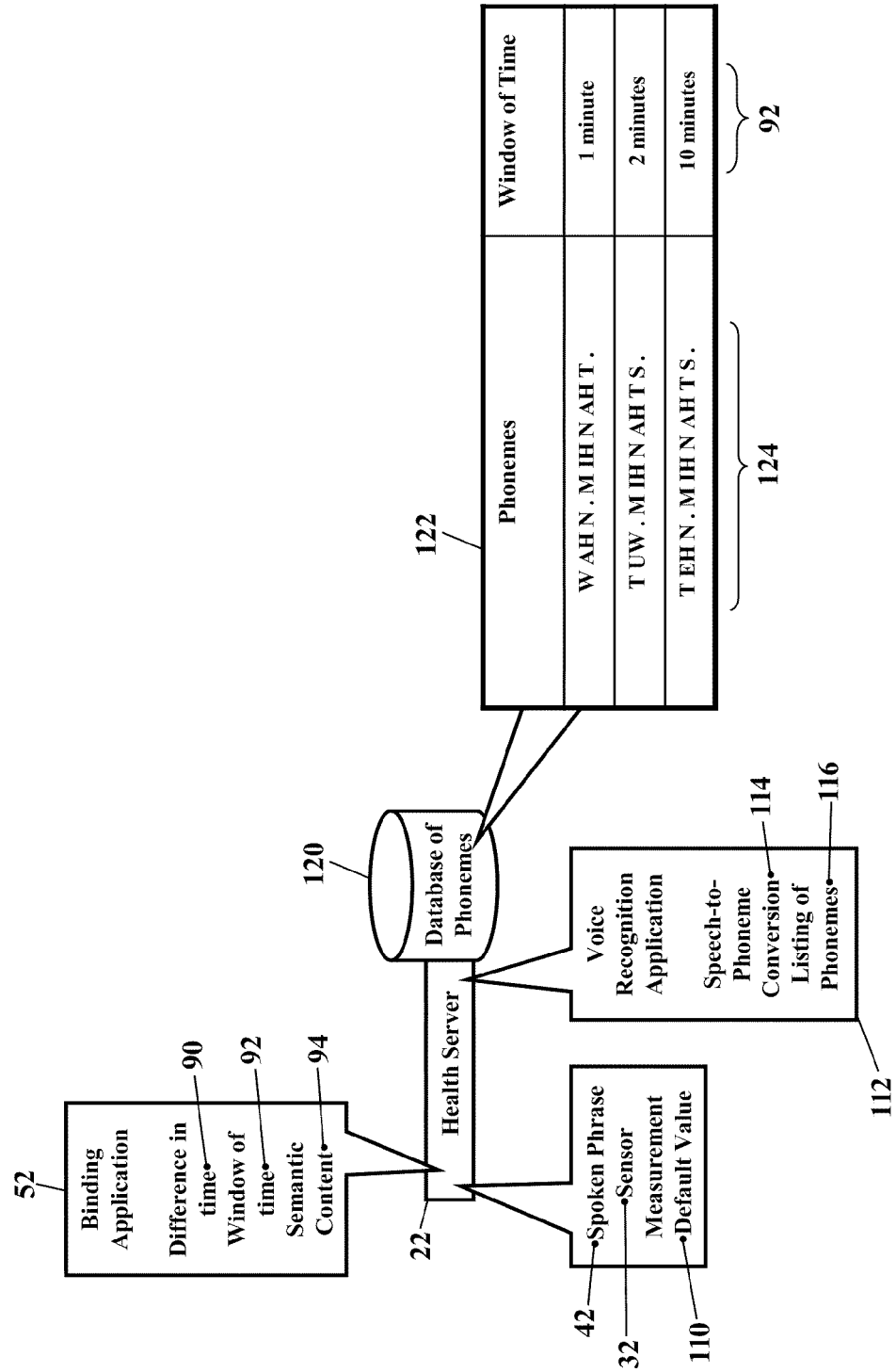

FIG. 5 illustrates phonetic recognition, according to exemplary embodiments. Here the voice-recognition application 112 may use phonetic recognition to determine the window 92 of time from the semantic content 94 of the spoken phrase 42. The voice-recognition application 112 receives the spoken phrase 42 as an input. The voice-recognition application 112 may then perform a speech-to-phoneme conversion 114 and output a listing 116 of phonemes that corresponds to the spoken phrase 42. The voice-recognition application 112 may then query a database 120 of phonemes for combinations that may be used to infer the window 92 of time. The database 120 of phonemes, for example, may store combinations of phonemes that may be commonly used to describe the window 92 of time. The database 120 of phonemes is illustrated as being locally stored in the memory (illustrated as reference numeral 54 in FIG. 2) of the health server 22, but the database 120 of phonemes may be remotely accessed via the communications network 24. The database 120 of phonemes is illustrated as a table 122 that maps, relates, or otherwise associates phonemes 124 to the window 92 of time. The database 120 of phonemes stores popular phoneme combinations for "one minute," "five minutes," or other terms and phrases that may describe the window 92 of time. If the listing 116 of phonemes contains a string or combination of the phonemes 124 that match an entry in the database 120 of phonemes, then the corresponding window 92 of time is retrieved. The binding application 52 then uses the window 92 of time when comparing the difference 90 in time between the time-stamped spoken phrase 42 and the time-stamped sensor measurement 32 (as earlier paragraphs explained).

Figure 6:
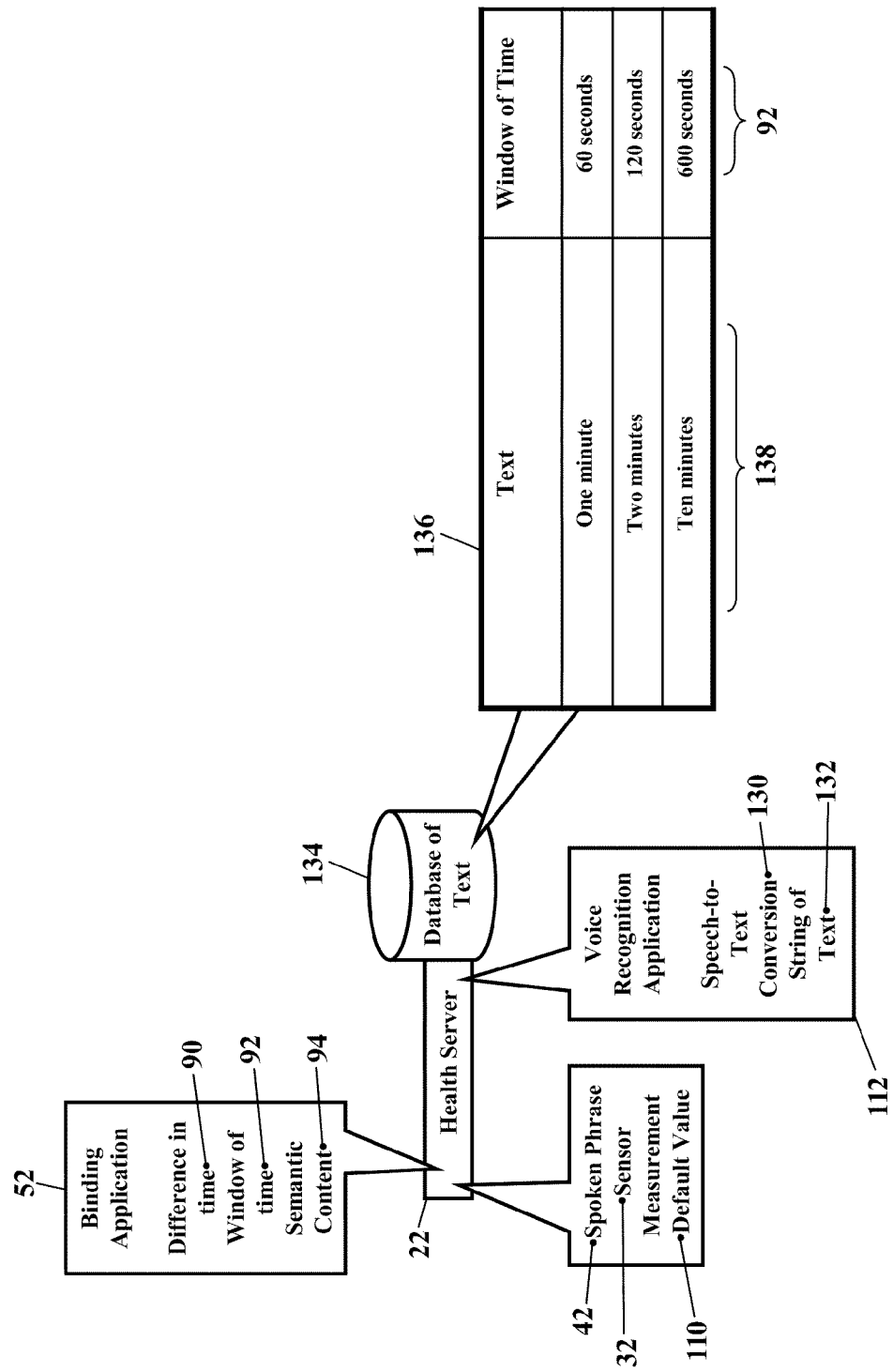

FIG. 6 illustrates text recognition, according to exemplary embodiments. Here the voice-recognition application 112 may use speech-to-text conversion to determine the window 92 of time. The voice-recognition application 112, as before, receives the spoken phrase 42 as an input. The voice-recognition application 112 may then perform a speech-to-text conversion 130 and output a string 132 of text that corresponds to the spoken phrase 42. The voice-recognition application 112 may then query a database 134 of text for textual combinations that may be used to infer the window 92 of time. The database 134 of text may store textual combinations that may be commonly used to describe the window 92 of time. The database 134 of text is illustrated as being locally stored in the health server 22, but the database 134 of text may be remotely accessed (perhaps via the communications network 24 illustrated in FIG. 1). The database 134 of text is illustrated as a table 136 that maps, relates, or otherwise associates textual combinations 138 to the window 92 of time. The database 134 of text stores popular textual combinations, such as "one minute," "five minutes," and other time-value terms and phrases (such as "three o'clock" or "five thirty"). If the string 132 of text contains a text string that matches an entry in the database 134 of text, then the corresponding window 92 of time is retrieved. The binding application 52 then uses the window 92 of time when comparing the difference 90 in time between the time-stamped spoken phrase 42 and the time-stamped sensor measurement 32 (as earlier paragraphs explained).

Figure 7:
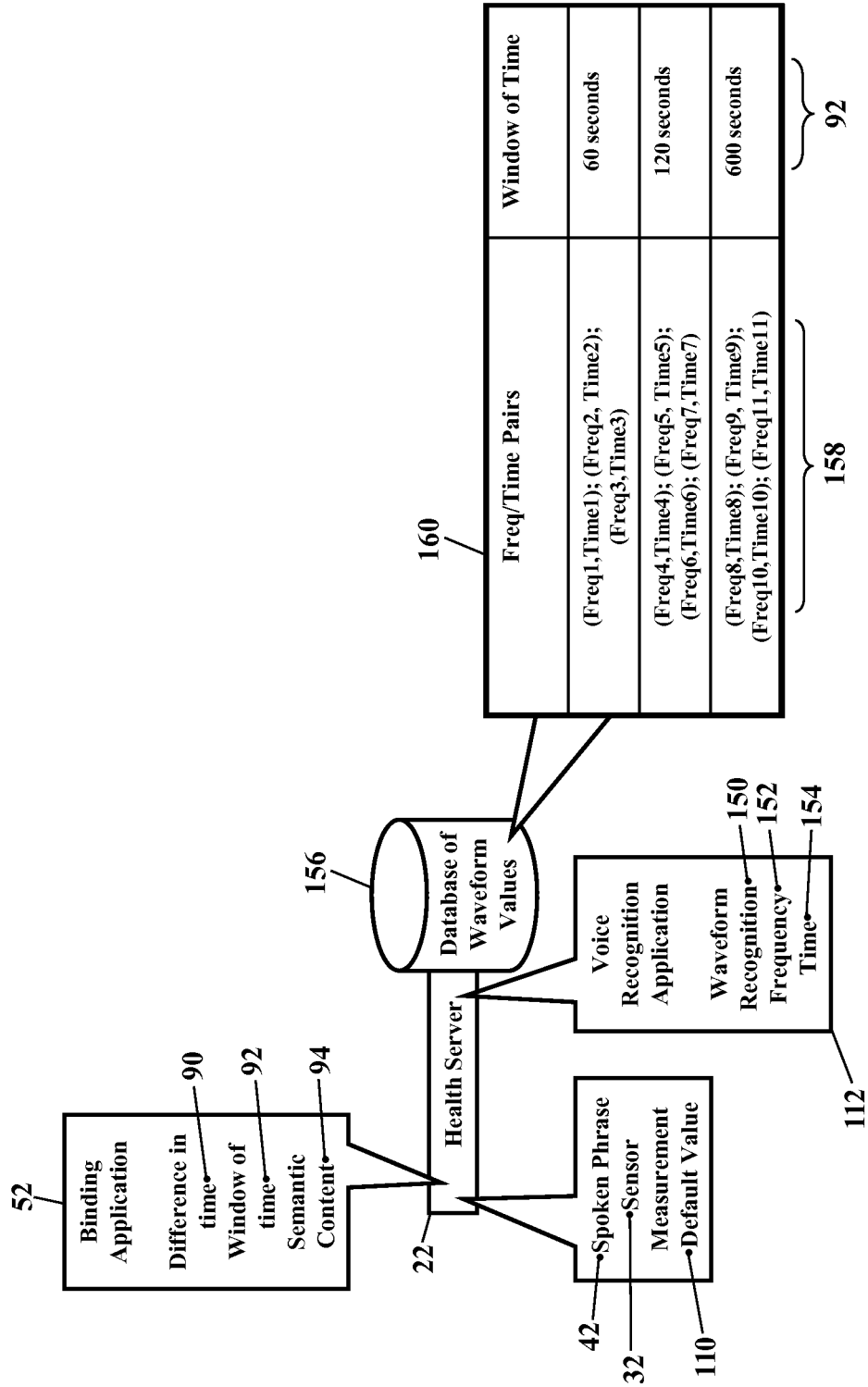

FIG. 7 illustrates waveform recognition, according to exemplary embodiments. Here the voice-recognition application 112 may use waveform recognition 150 to determine the window 92 of time. The voice-recognition application 112 again receives the spoken phrase 42 as an input. The spoken phrase 42, however, may be represented by, or converted into, pair values of frequency 152 and time 154. The frequency 152 and corresponding time 154 values may be compared to a database 156 of waveform values. The database 156 of waveform values stores frequency/time pairings 158 for the waveforms describing common time-value terms and phrases (again, "one minute," "five minutes," and "ten minutes"). The database 156 of waveform values is illustrated as being locally stored in the health server 22, but the database 156 of waveform values may be remotely accessed. The database 156 of waveform values is illustrated as a table 160 that maps, relates, or otherwise associates frequency/time pairings 158 to the window 92 of time. If the pair values 158 of frequency and time match an entry in the database 156 of waveform values, then the corresponding window 92 of time is retrieved. The binding application 52 then uses the window 92 of time when comparing the time-stamped spoken phrase 42 and the time-stamped sensor measurement 32 (as earlier paragraphs explained).

Figure 8:
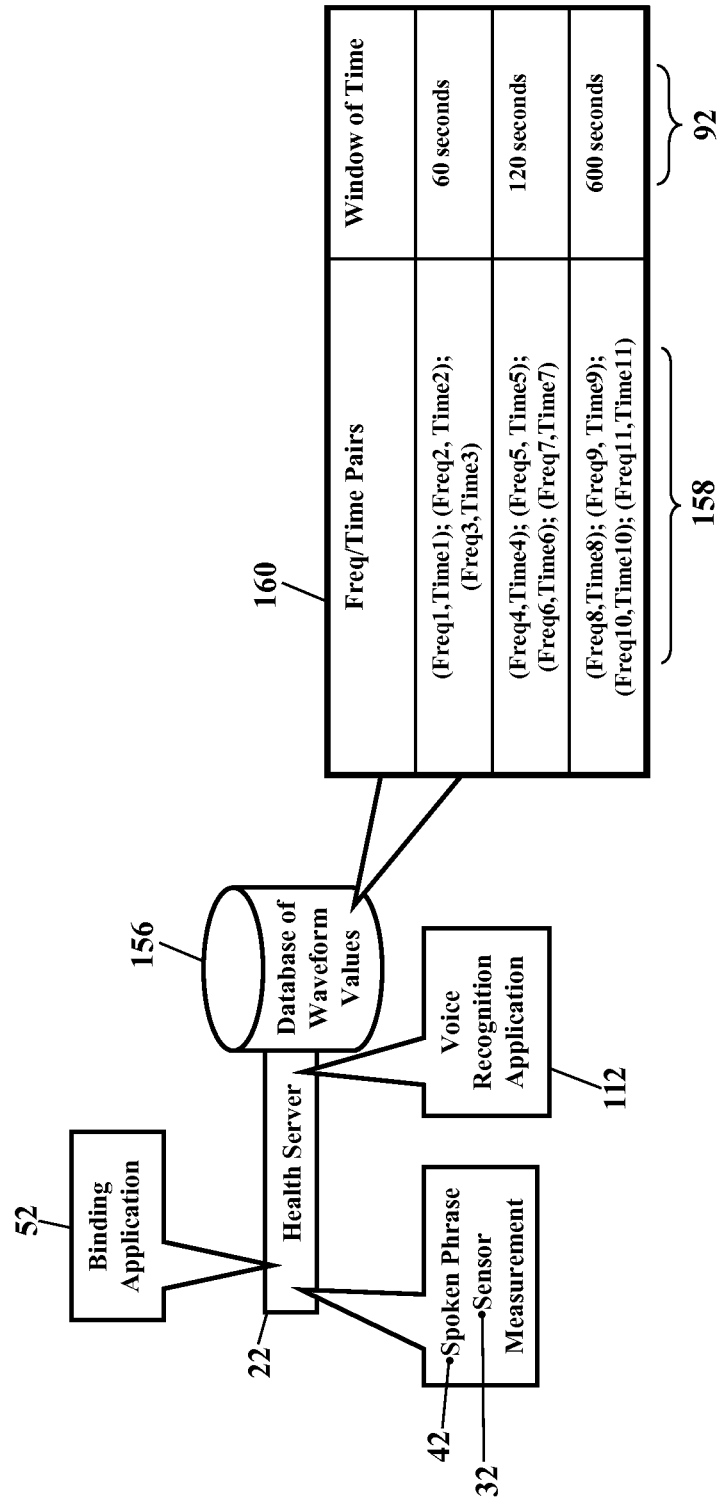
FIG. 8 is a schematic illustrating voice recognition of the spoken phrase, according to exemplary embodiments.

FIG. 8 is a schematic illustrating voice recognition of the spoken phrase 42, according to exemplary embodiments. Here voice recognition may be used to determine the identity of the user who spoke the spoken phrase 42. When the binding application 52 receives the spoken phrase 42, the binding application 52 may call or invoke the voice-recognition application 112 to determine the user associated with the spoken phrase 42. The voice-recognition application 112 may use any of many known voice-recognition concepts to associate the spoken phrase 42 to a particular user. Once the appropriate user is identified from the spoken phrase 42, the binding application 52 may then accurately associate the identified user to the sensor measurement 32 in the database 34 of health information. Because voice recognition is well known, this disclosure need not further discuss voice-recognition of the spoken phrase 42.

Figure 9:
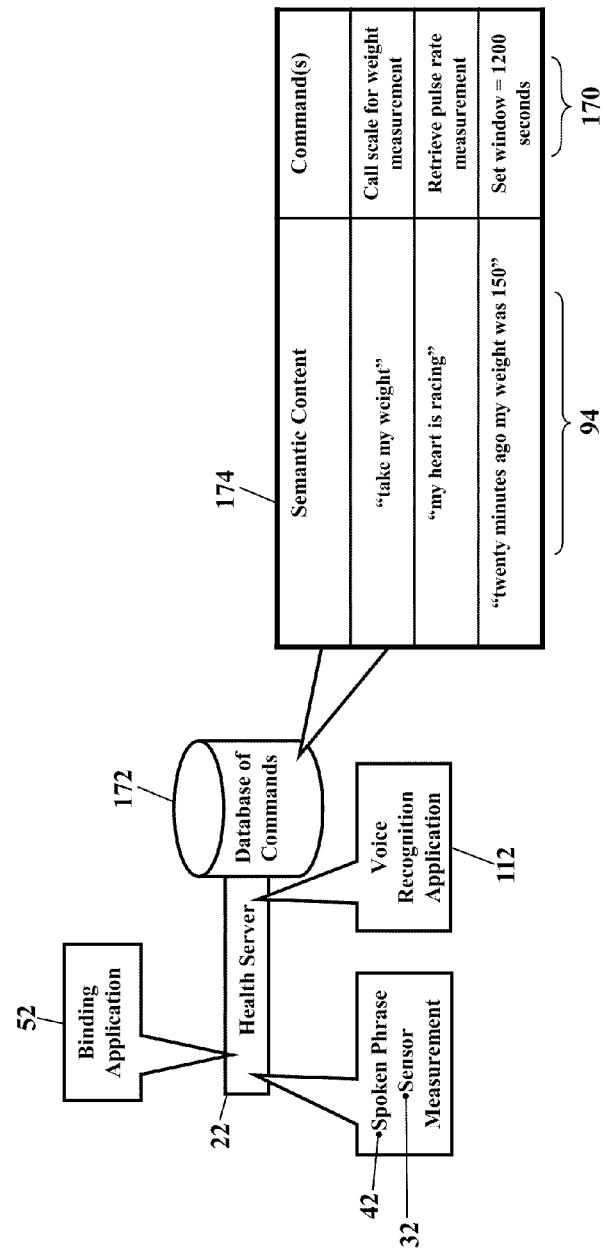
FIG. 9 is a schematic illustrating voice recognition of commands, according to exemplary embodiments.

FIG. 9 is a schematic illustrating voice recognition of commands, according to exemplary embodiments. When the binding application 52 receives the spoken phrase 42, the voice-recognition application 112 may be used to execute a command or phrase contained within the spoken phrase 42. The voice-recognition application 112 may use any of many known voice-recognition concepts to associate the spoken phrase 42 to a particular command 170. The voice-recognition application 112, for example, may be used to recognize pre-registered commands (e.g., "turn on bathroom scale" or "take my blood pressure"). The voice-recognition application 112 may use speech-to-phoneme conversion, speech-to-text conversion, and/or waveform recognition (illustrated, respectively, with reference to FIGS. 5-7) to determine one or more commands 170 from the semantic content 94 of the spoken phrase 42. The semantic content 94 may then be compared to a database 172 of commands. The database 172 of commands is illustrated as being locally stored in the health server 22, but the database 172 of commands may be remotely accessed. The database 172 of commands is also illustrated as a table 174 that maps, relates, or otherwise associates the semantic content 94 to commands 170. If the semantic content 94 of the spoken phrase 42 matches an entry in the database 172 of commands, then the corresponding command 170 is retrieved. The binding application 52 may then instruct the health server 22 to execute the command 170.

Figure 10:
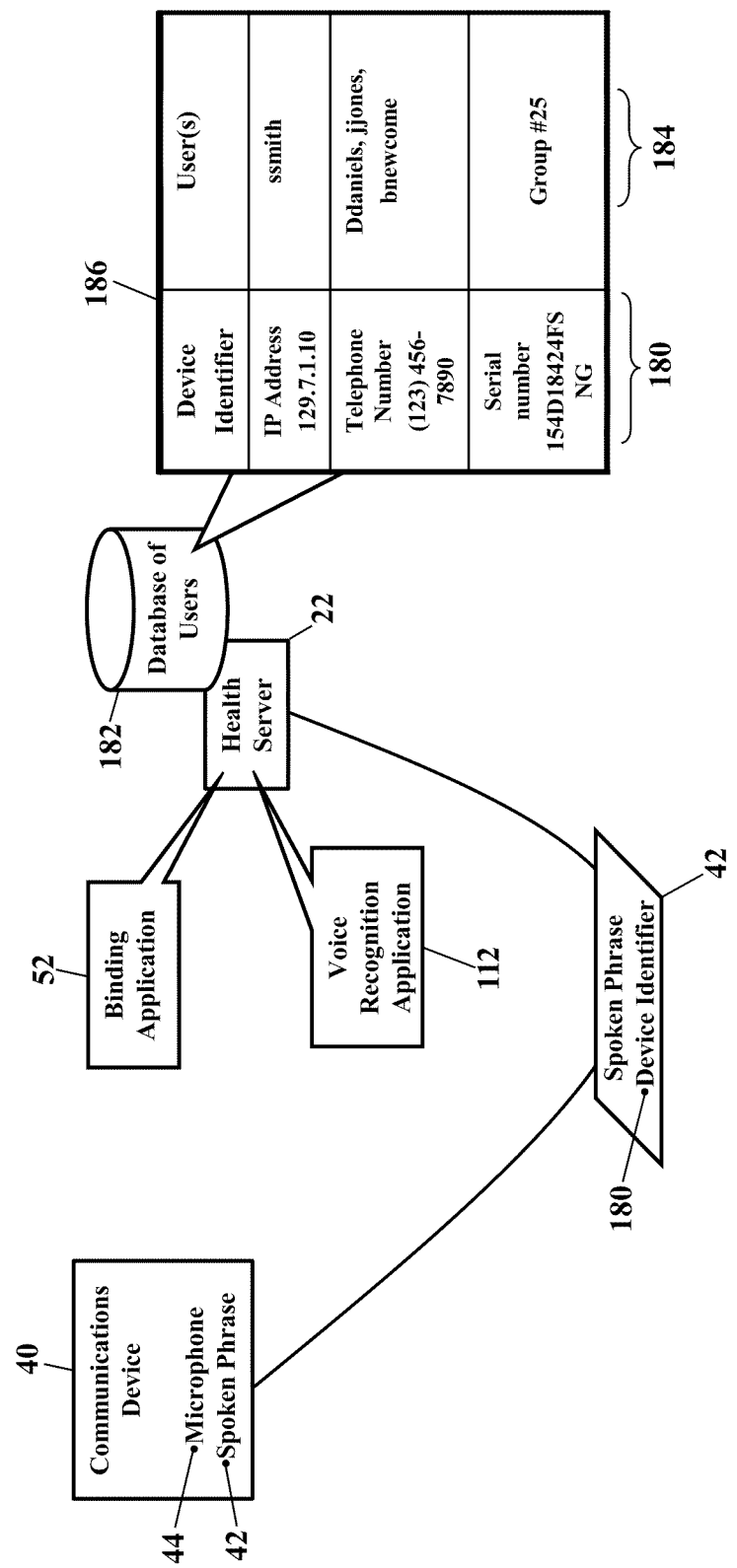
FIG. 10 is a schematic illustrating a device identifier, according to exemplary embodiments.

FIG. 10 is a schematic illustrating a device identifier 180, according to exemplary embodiments. When the health server 22 receives the spoken phrase 42 from the user's communications device 40, the spoken phrase 42 may include the device identifier 180. The device identifier 180 uniquely identifies the communications device 40 that received or sent the spoken phrase 42. The device identifier 180 may be a serial number, Internet Protocol address, telephone number, or any other alphanumeric combination. When the health server 22 receives the device identifier 180, the binding application 52 may use the device identifier 180 to help identify the user who input the spoken phrase 42 into the communications device 40.

The binding application 52 may then query a database 182 of users. The database 182 of users stores associations between device identifiers 180 and users 184. Once the device identifier 180 is known, the database 182 of users may reveal a single user, or a group of users, that are associated with the communications device 40. If multiple users share the same communications device 40 (such as a cell phone, PDA, or remote control), then the multiple users may be associated to the device identifier 180 of the shared communications device 40. The database 182 of users, for example, is illustrated as being locally stored in the the health server 22, but the database 182 of users may be remotely accessed. The database 182 of users is illustrated as a table 186 that maps, relates, or otherwise associates the device identifier 180 to one or more users 184. The binding application 52 queries the database 182 of users for the device identifier 180 and retrieves the user, or group of users, that are associated with the communications device 40. When the binding application 52 attempts to identify a specific user from the spoken phrase 42 (as earlier paragraphs explained), the binding application 52 may reduce the pool of candidates to those users associated with the device identifier 180. The voice recognition application 112, for example, may much more quickly match the spoken phrase 42 to the correct user. Instead of trying to match the spoken phrase 42 to a pool of hundreds or thousands of possible candidates, the binding application 52 may substantially reduce the pool to only those users associated with the device identifier 180 and, thus, the communications device 40.

Figure 11:
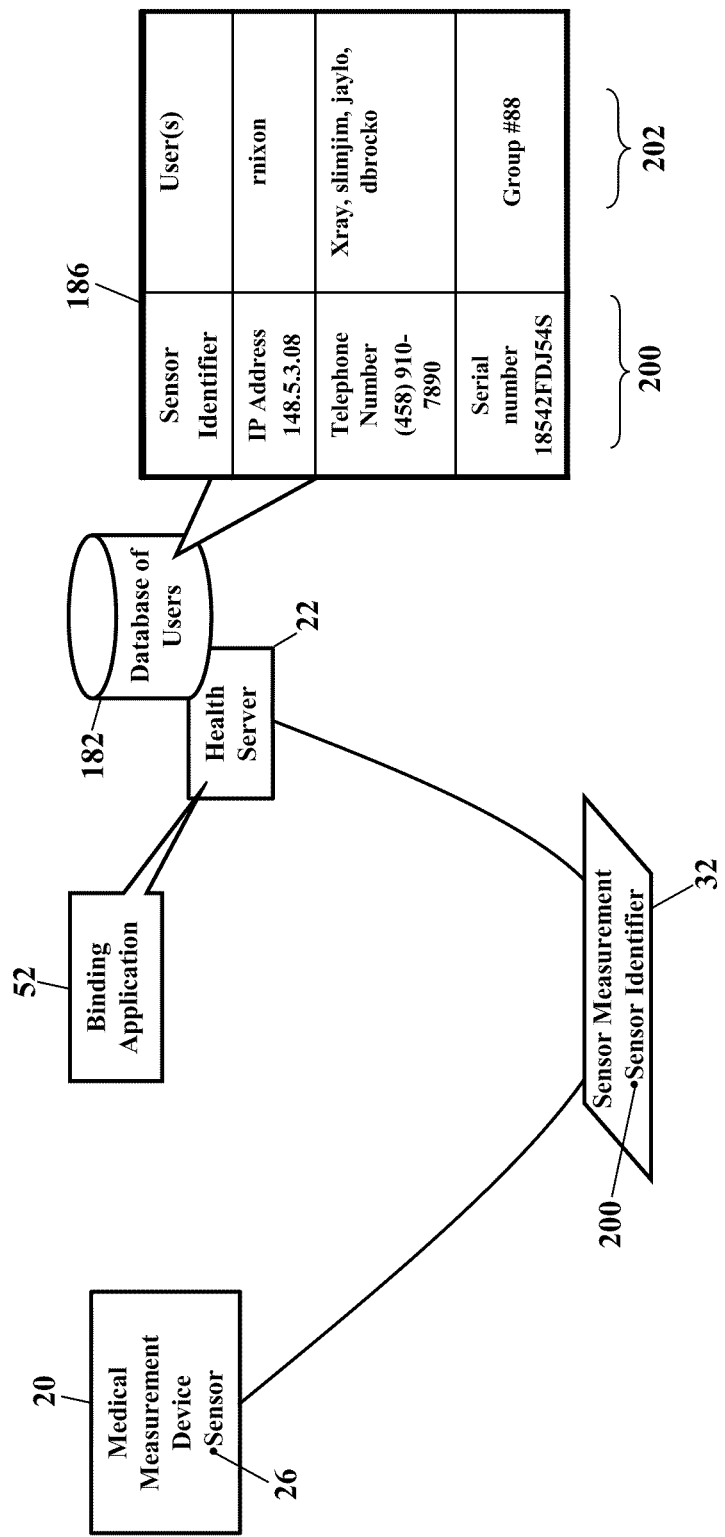
FIG. 11 is a schematic illustrating a sensor identifier, according to exemplary embodiments.

FIG. 11 is a schematic illustrating a sensor identifier 200, according to exemplary embodiments. When the health server 22 receives the sensor measurement 32 from the medical measurement device 20, the sensor measurement 32 may include the sensor identifier 200. The sensor identifier 200 uniquely identifies the medical measurement device 20, and/or the sensor 26, that sent the sensor measurement 32. The sensor identifier 200 may be a serial number, Internet Protocol address, telephone number, or any other alphanumeric combination. When the health server 22 receives the sensor identifier 200, the binding application 52 may use the sensor identifier 200 to help identify the user who spoke the spoken phrase 42.

The binding application 52 may then query the database 182 of users. Here the database 182 of users also stores associations between sensor identifiers 200 and users 202. Once the sensor identifier 200 is known, the database 182 of users may reveal a single user, or a group of users, that are associated with the sensor identifier 200. The binding application 52 queries the database 182 of users for the sensor identifier 200 and retrieves the associated user or group of users. The sensor identifier 200 again permits the binding application 52 to reduce the pool of candidates to those users associated with the sensor identifier 200. So, instead of trying to match the spoken phrase 42 to one of hundreds or thousands of possible candidates, the pool of candidates may be reduced to only those users associated with the sensor identifier 200 and/or the device identifier 180.

Figure 12:
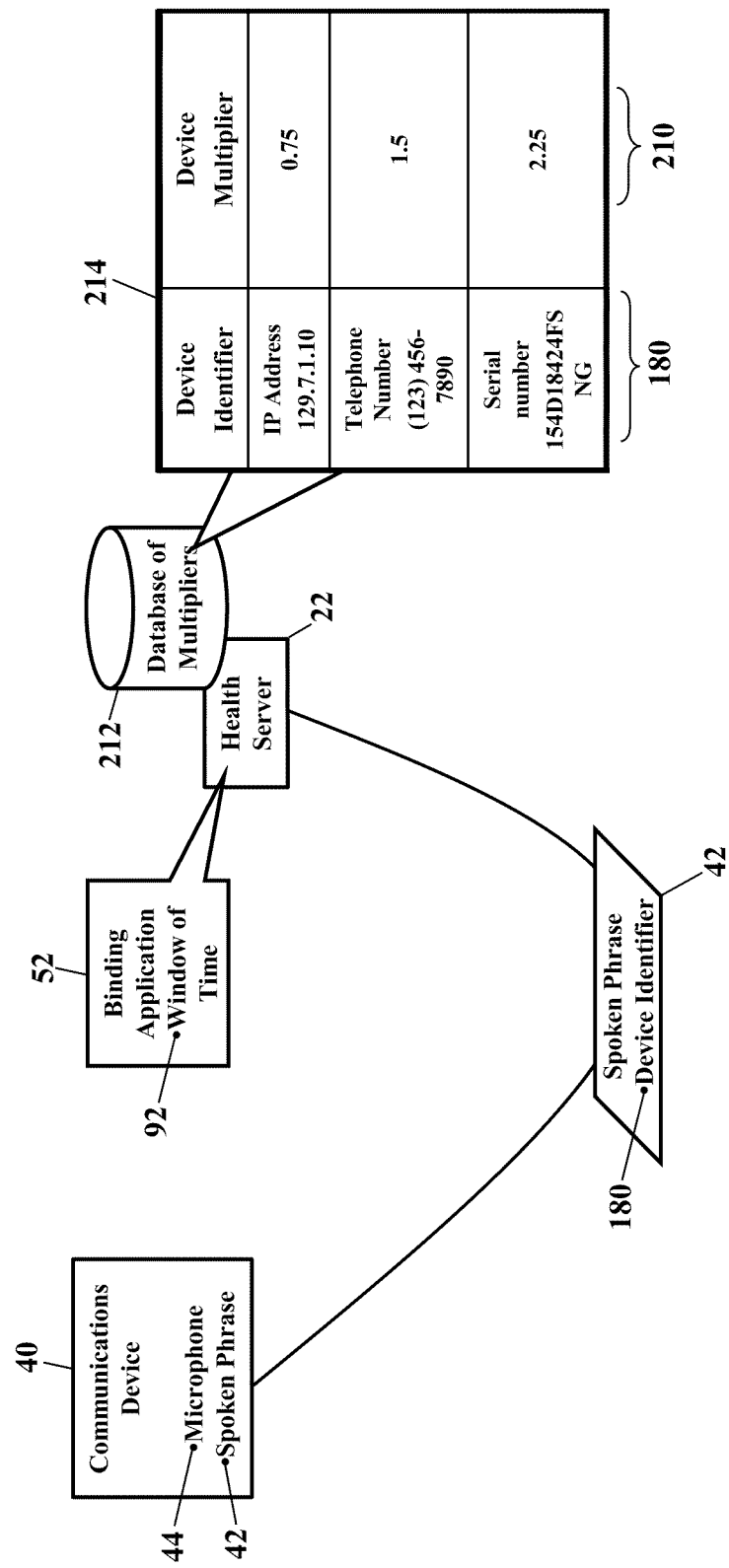
FIGS. 12-13 are more detailed schematics illustrating the operating environment, according to exemplary embodiments.
Figure 13:
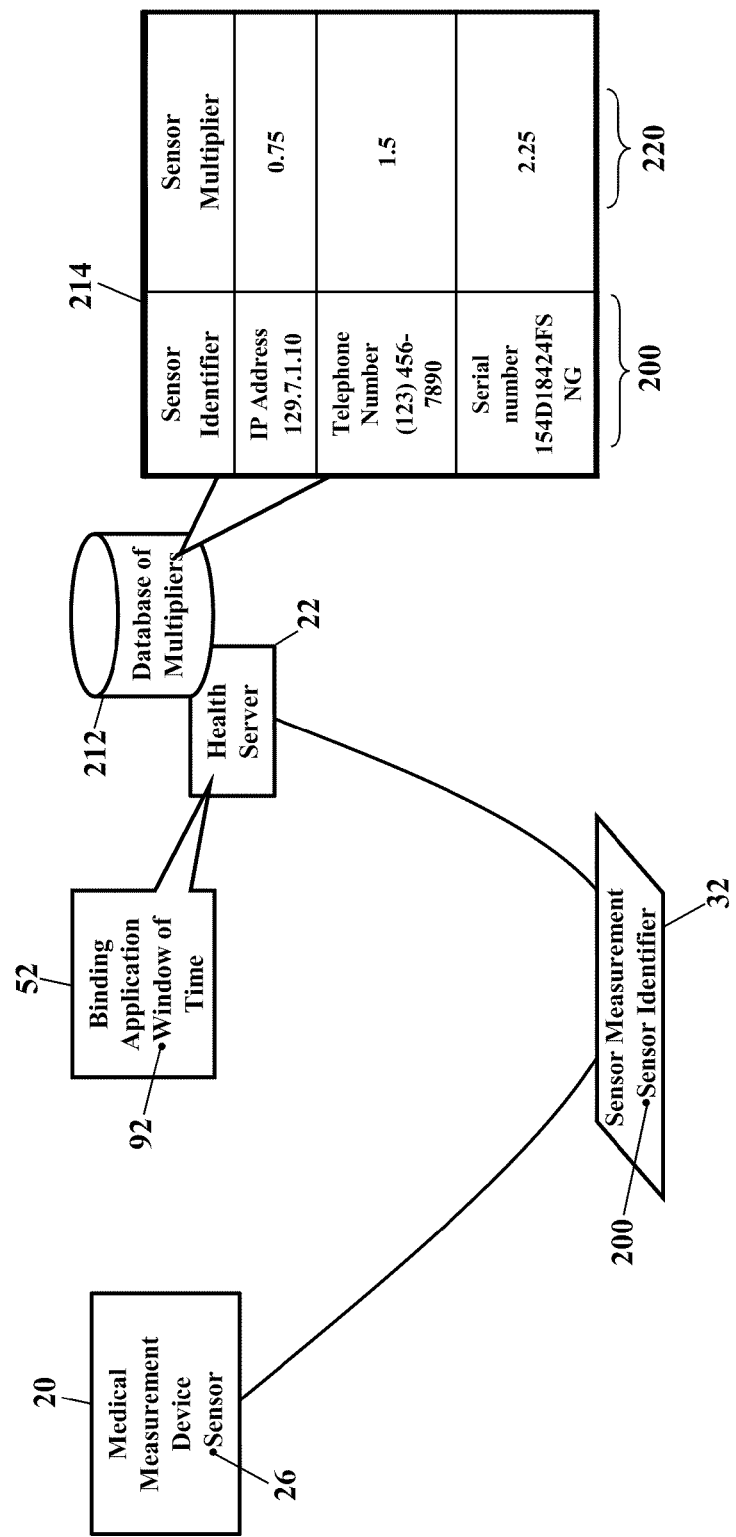

FIGS. 12-13 are more detailed schematics illustrating the operating environment, according to exemplary embodiments. Here multipliers may be used to expand, or contract, the window 92 of time. FIG. 12, for example, illustrates a device multiplier 210 that may be associated to the device identifier 180, according to exemplary embodiments. The device multiplier 210 may be a multiplication factor that increases, or decreases, the window 92 of time. The window 92 of time, in other words, may be increased, or decreased, based on the communications device 40 that sent the spoken phrase 42. Suppose, for example, that the device identifier 180 reveals that the user's communications device 40 has a large form-factor keypad. The keys of the keypad are enlarged for easier identification and depression. These enlarged keys may indicate that the user has reduced eyesight or physical capabilities. The device multiplier 210, then, may be used to expand the window 92 of time. If the device identifier 180 indicates that the user may need additional time to perfect the binding, then the window 92 of time may be adjusted to provide more time.

The binding application 52 may thus query a database 212 of multipliers. The database 212 of multipliers stores associations between device identifiers 180 and device multipliers 210. Once the device identifier 180 is known, the database 212 of multipliers may be queried for the corresponding device multiplier 210. The database 212 of multipliers is illustrated as being locally stored in the health server 22, but the database 212 of multipliers may be remotely accessed. The database 212 of multipliers is illustrated as a table 214 that maps, relates, or otherwise associates the device identifier 180 to the corresponding device multiplier 210. The binding application 52 queries the database 212 of multipliers for the device identifier 180 and retrieves the corresponding device multiplier 210. The binding application 52 may then increase, or decrease, the window 92 of time based on the device multiplier 210. If the window 92 of time is one minute (60 seconds), for example, and the device multiplier 210 is 1.5, then the final window 92 of time is (60 seconds)×(1.5)=90 seconds.

Conversely, should the device identifier 180 indicate that the communications device 40 is an APPLE® IPHONE® or other "smart" device, then the user may be proficient and skilled at binding their sensor measurement 32 to their spoken phrase 42. In this case, then, the device multiplier 210 may actually reduce the window 92 of time in order to permit more users to more quickly share the medical measurement device 20. Again, if the window 92 of time is one minute (60 seconds), but the device multiplier 210 is 0.75, then the final window 92 of time is (60 seconds)×(0.75)=45 seconds.

FIG. 13 illustrates a sensor multiplier 220, according to exemplary embodiments. The sensor multiplier 220 may also be used to increase, or decrease, the window 92 of time. Here, though, the sensor multiplier 220 may be associated with the sensor identifier 200 that sent the sensor measurement 32. If some characteristic related to the sensor 26 and/or the medical measurement device 20 justifies adjusting the window 92 of time, then the sensor multiplier 220 may be used. Again, if the sensor identifier 200 indicates that the sensor 26 and/or the medical measurement device 20 is registered to an elderly person, then that elderly person may need additional time to perfect the binding. The sensor multiplier 220 may thus be used to increase the window 92 of time to provide more time. If the sensor identifier 200 indicates that the sensor 26 and/or the medical measurement device 20 is registered to a proficient user, then the sensor multiplier 220 may be less than one (1) to reduce the window 92 of time.

Figure 14:
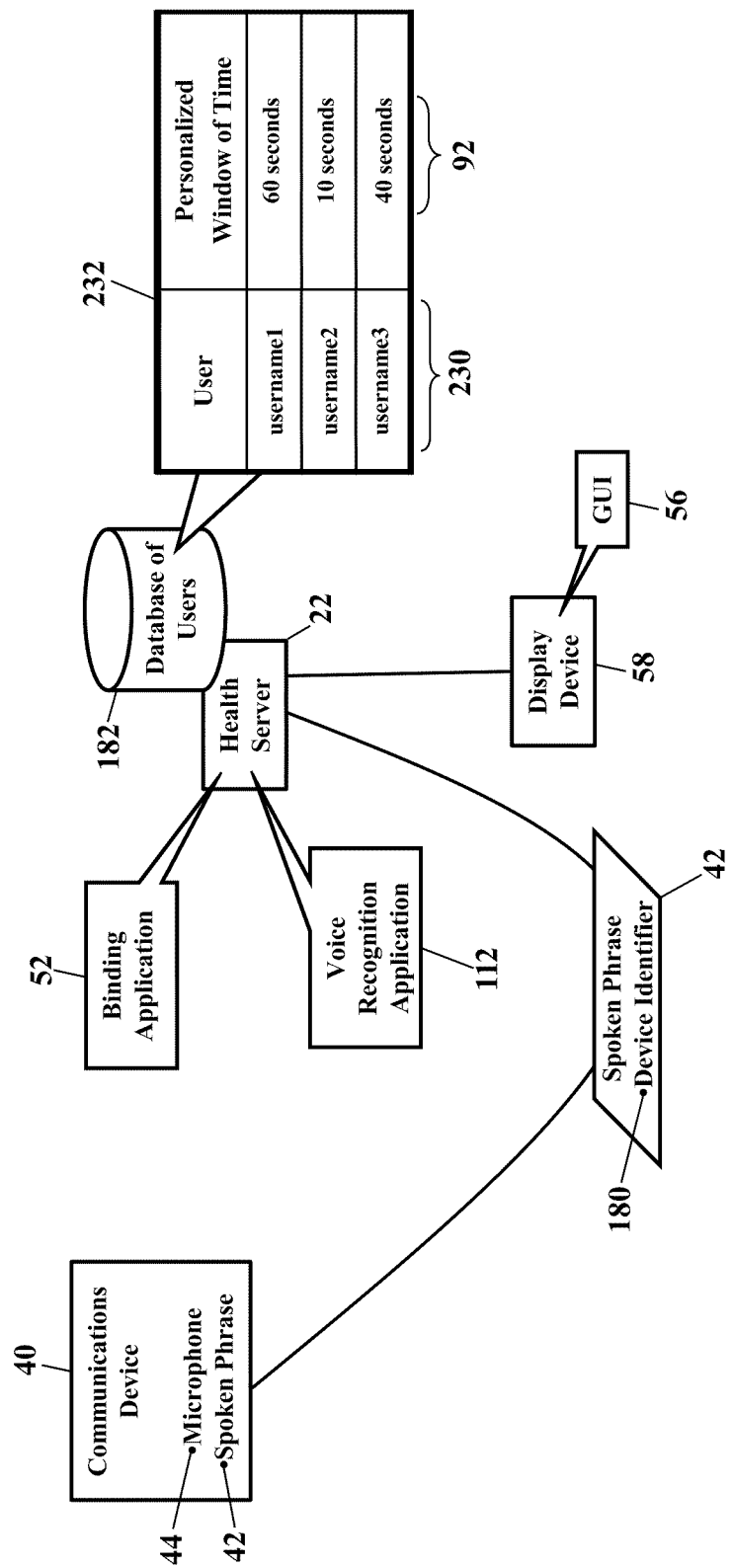
FIGS. 14-15 are schematics illustrating personalized windows of time, according to exemplary embodiments.

FIG. 14 is a schematic illustrating personalized windows of time, according to exemplary embodiments. Here each individual user may determine and configure a unique window 92 of time. The window 92 of time, in other words, may be associated with the user identified from the spoken phrase 42. Exemplary embodiments may thus permit each user to configure and personalize the window 92 of time, based on the user's individual characteristics or capabilities. If the user is proficient, then the user may want a short window 92 of time. If a different user desires more time to perfect the binding, then the window 92 of time may be longer for that user. The window 92 of time may thus be configurable to suit each user's desires.

FIG. 14 further illustrates the database 182 of users. The database 182 of users stores associations between users 230 and the window 92 of time. Once the user 230 is identified from the spoken phrase 42, the database 182 of users may be queried for the corresponding window 92 of time. The database 182 of users is illustrated as being locally stored in the health server 22, but the database 182 of users may be remotely accessed. The database 182 of users is illustrated as a table 232 that maps, relates, or otherwise associates a user 230 to the corresponding window 92 of time. The binding application 52 queries the database 182 of users for the identified user 230 and retrieves the corresponding window 92 of time. The binding application 52 may then use the window 92 of time when comparing the difference 90 in time between the sensor measurement 32 and the spoken phrase 42 (as earlier paragraphs explained).

The graphical user interface 56 may be used to input the personalized window 92 of time. The graphical user interface 56 may include one or more visual and/or audible prompts for personalizing the window 92 of time. The graphical user interface 56 may include one or more data fields for entry of a user's personalized window 92 of time. Once a user inputs their desired window 92 of time, then the user's personalized window 92 of time may be stored and referenced in the database 182 of users.

Figure 15:
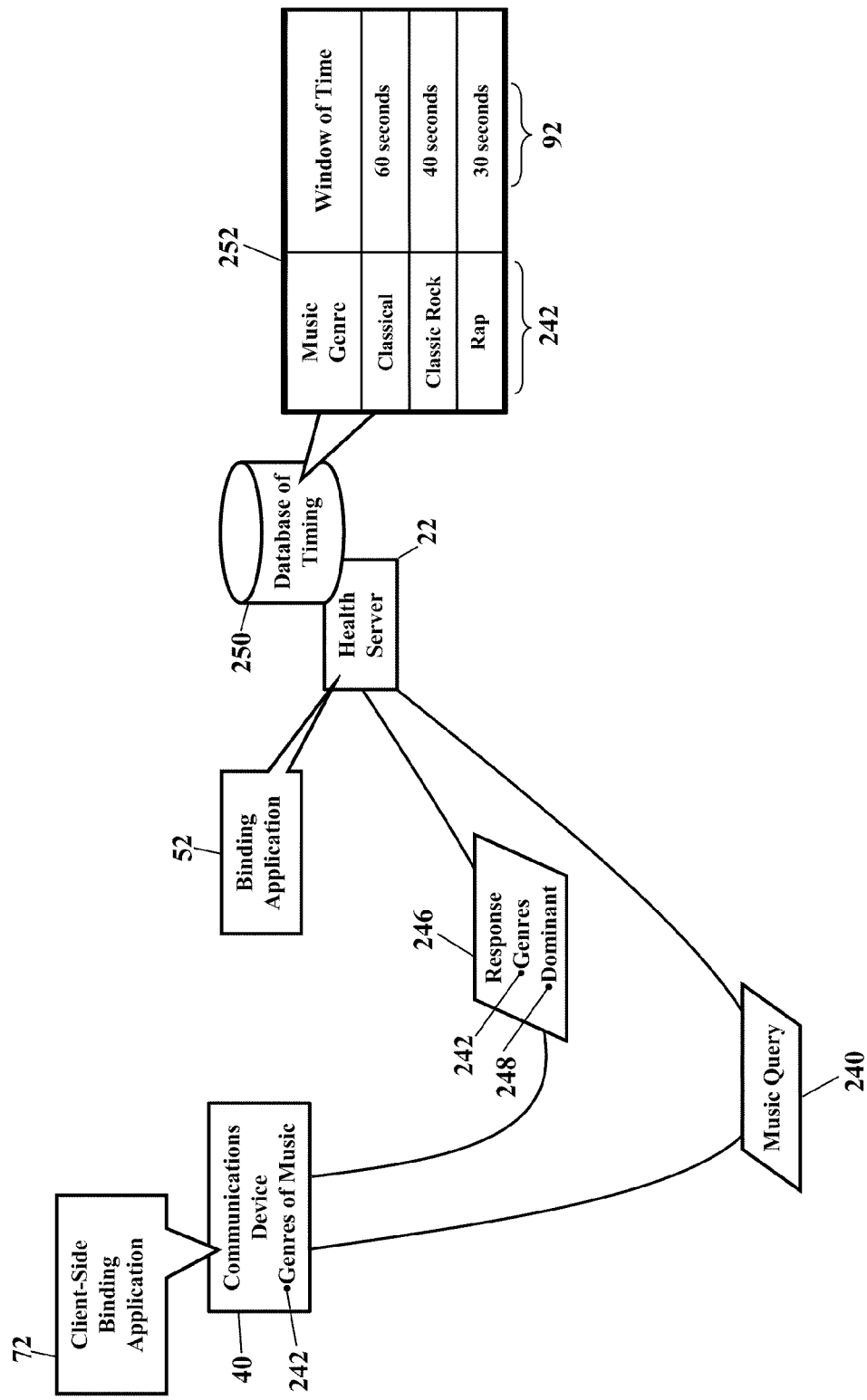

FIG. 15 is another schematic illustrating personalized windows of time, according to exemplary embodiments. Here the window 92 of time may also be determined from a user's music selections. The binding application 52 may query the user's communications device 40 for genres of music stored and/or played by the communications device 40. The age of the user may be inferred from the genres of music, and the length of the window 92 of time may then be adjusted based on the user's age. The window 92 of time, in other words, may be at least partially derived from the genres of music enjoyed by the user. Rap music may indicate a younger and more proficient user, so the window 92 of time may be reduced (perhaps to a minimum value). Classic rock may indicate a member of the "baby boomer" generation, so the window 92 of time may be increased to a middle value. 1940s and 1950s music may indicate seniors and elderly, so the window 92 of time may be expanded to a maximum value. The window 92 of time may be further refined by "decades" music, such as 70s, 80s, and 90s hits that may more accurately indicate the user's age.

FIG. 15 thus illustrates a music query 240. When the health server 22 communicates with the user's communications device 40, the binding application 52 may communicate with the client-side binding application 72 stored in the user's communications device 40. The binding application 52 and the client-side binding application 72 cooperate to determine the genres 242 of music that are stored by, and/or played by, the communications device 40. The binding application 52 causes the processor in the health server 22 to send the music query 240. The music query 240 communicates to an address associated with the user's communications device 40. When the user's communications device 40 receives the music query 240, the client-side binding application 52 causes the client processor (illustrated as reference numeral 80 in FIG. 2) in the user's communications device 40 to determine the genres 242 of music stored and/or played by the communications device 40. If the user's communications device 40 stores or plays multiple genres, then the client-side binding application 52 may determine which genre is most played or enjoyed in time. The client-side binding application 52, for example, may determine that "90s hits" are cumulatively played or executed more than any other genre.

The client-side binding application 52 may send a response 246. The response 246 may include information related to the genres 242 of music stored and/or played by the communications device 40. More particularly, the response 246 may identify a dominant genre 248 achieving the most playing time. When the health server 22 receives the response 246, the binding application 52 retrieves the genres 242 of music stored and/or played by the communications device 40 and/or the dominant genre 248 having the greatest cumulative playing time.

The binding application 52 may then consult a database 250 of timing. The database 250 of timing information stores associations between the genres 242 of music and the window 92 of time. Once the user's music selections are identified, the database 250 of timing information may be queried for the corresponding window 92 of time. The database 250 of timing information is illustrated as being locally stored in the health server 22, but the database 250 of timing information may be remotely accessed. The database 250 of timing information is illustrated as a table 252 that maps, relates, or otherwise associates the genres 242 of music to the corresponding window 92 of time. The binding application 52 queries the database 250 of timing information for the genres 242 of music and retrieves the corresponding window 92 of time. The binding application 52 may then use the window 92 of time when comparing the difference 90 in time between the sensor measurement 32 and the spoken phrase 42 (as earlier paragraphs explained).

Few user, though, have a single genre of music in their music selection. Most users have many genres of music, and each genre is enjoyed at different times. The binding application 52, then, may blend windows of time when multiple genres of music are identified. This blending may correspond to the cumulative times for each genre of music. Again referring to FIG. 15, suppose classical music is dominate and enjoyed 60% of the total playing time, while classic rock is 20% and rap is 20%. The binding application 52, then, may blend their windows 92 of time to obtain a final value for the window 92 of time according to final window of time=[(0.6)×(60 seconds)]+[(0.2)×(40 seconds)]+[(0.2)×(40 seconds)], or final window of time=52 seconds.

Here, then, the final value for the window 92 of time is proportional to the cumulative playing time for each genre of music. The binding application 52 may then use the final value (e.g., 52 seconds) for the window 92 of time when comparing the difference 90 in time between the sensor measurement 32 and the spoken phrase 42 (as earlier paragraphs explained).

Figure 16:
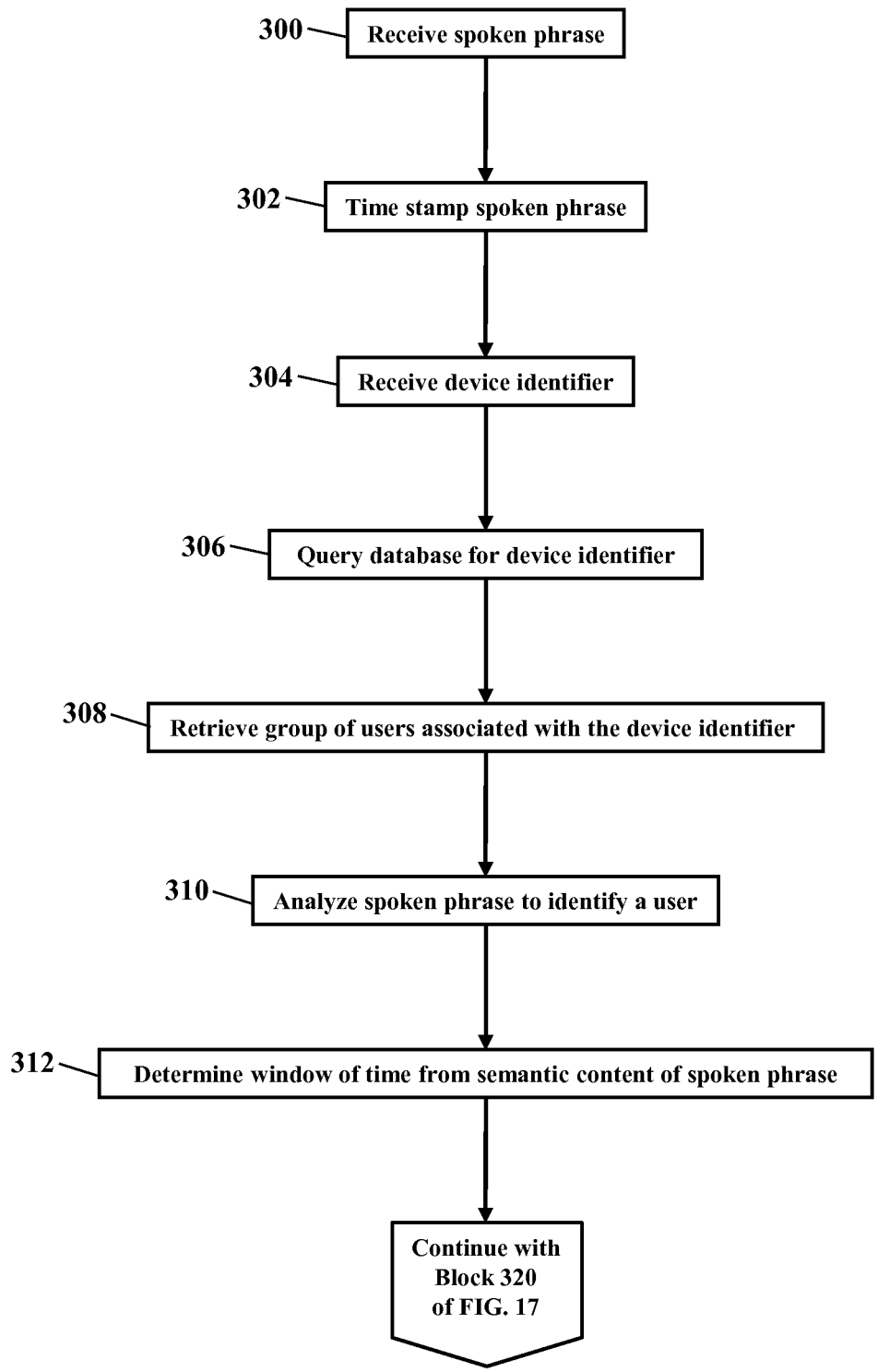
FIGS. 16-18 are flowcharts illustrating a method of measuring health, according to exemplary embodiments.
Figure 17:
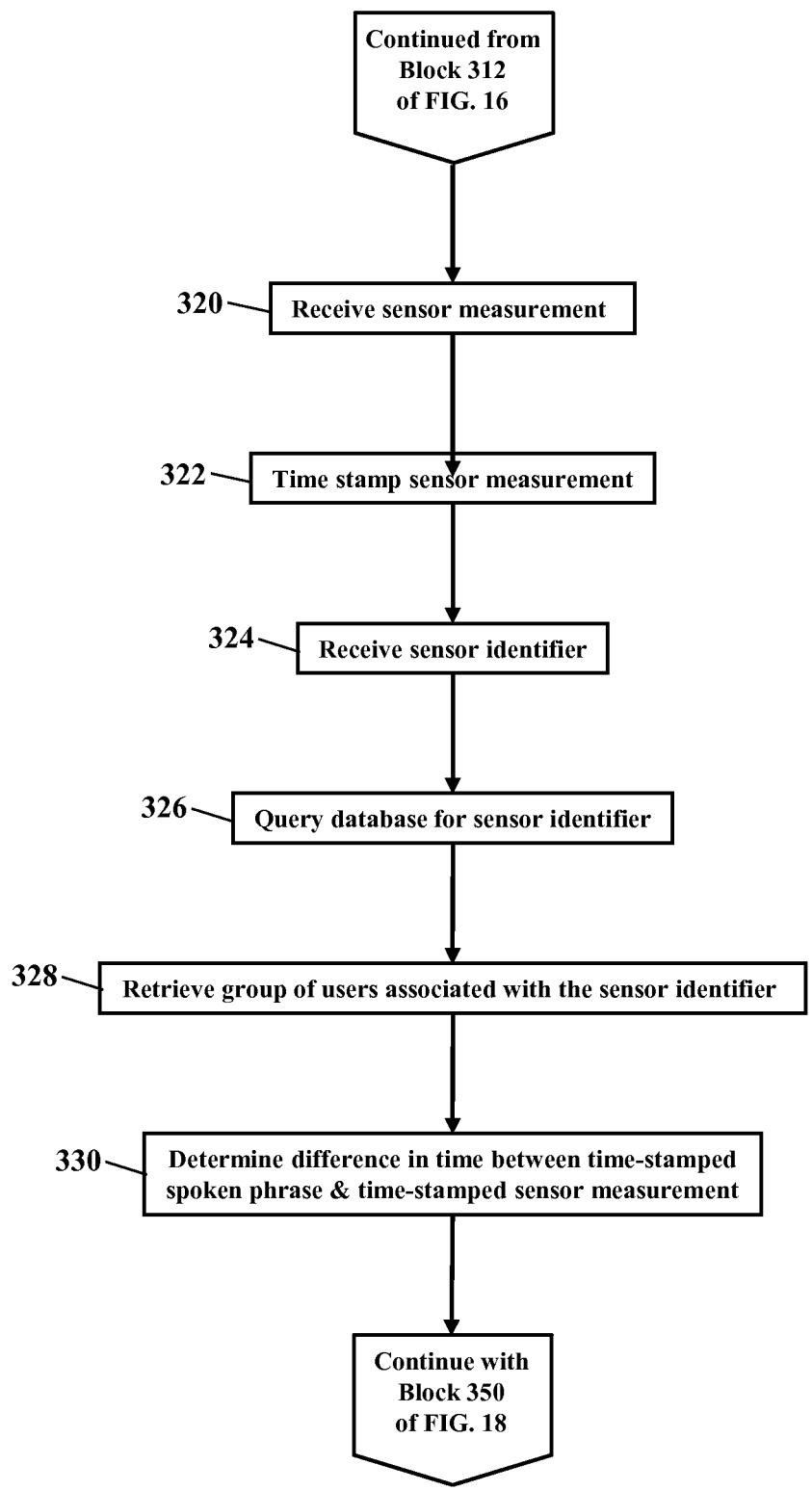
Figure 18:
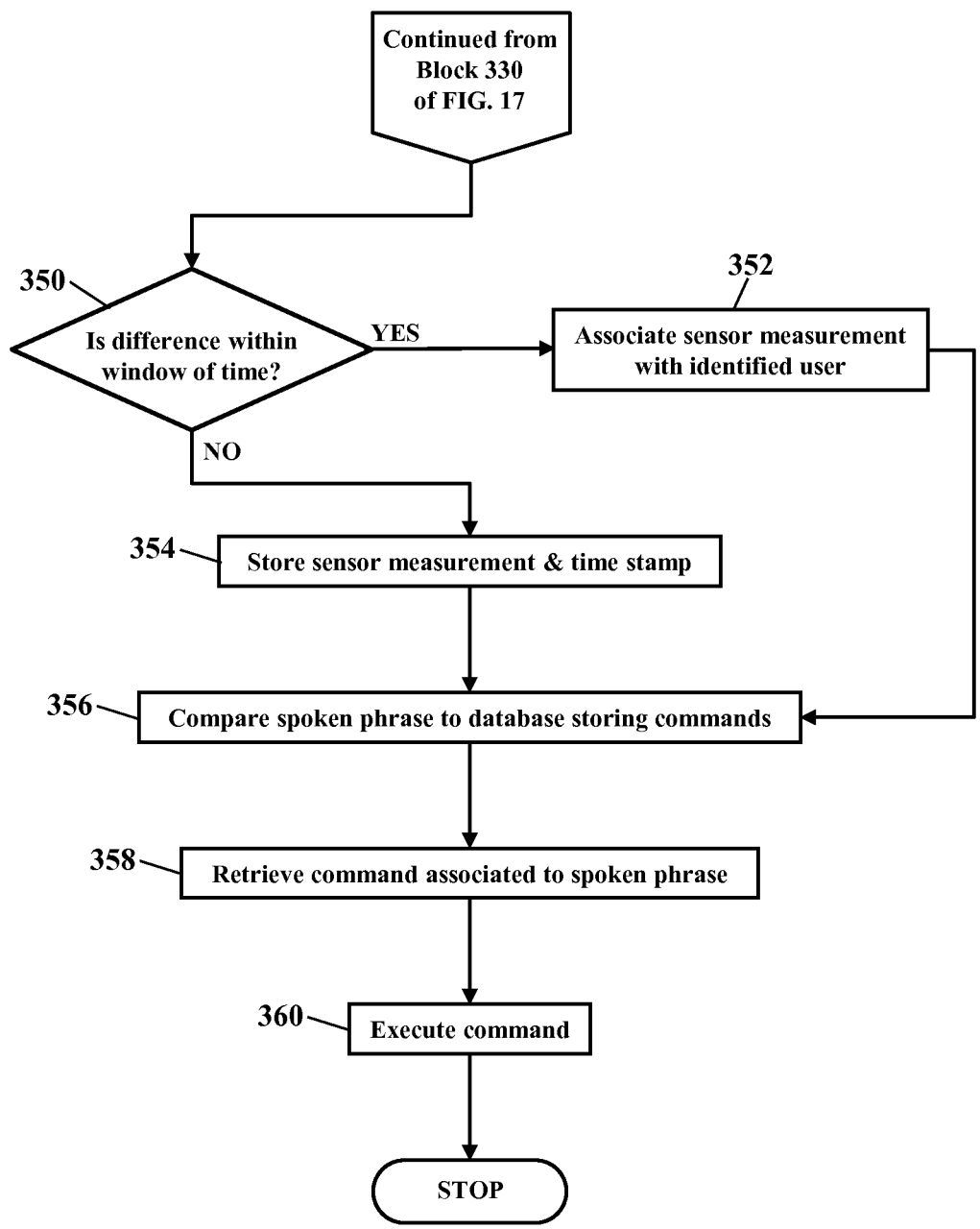

FIGS. 16-18 are flowcharts illustrating a method of measuring health, according to exemplary embodiments. An analog or digitized spoken phrase is received (Block 300) and time-stamped (Block 302). A device identifier, associated with a device that recorded the spoken phrase, is also received (Block 304). A database is queried for the device identifier (Block 306) and a group of users associated with the device identifier is retrieved (Block 308). The spoken phrase is analyzed to identify a user who spoke the spoken phrase (Block 310). A window of time is determined from a semantic content of the spoken phrase (Block 312).

The flowchart continues with FIG. 17. A sensor measurement is received (Block 320) and time-stamped (Block 322). A sensor identifier, associated with a sensor that measured the sensor measurement, is also received (Block 324). A database is queried for the sensor identifier (Block 326) and a group of users associated with the sensor identifier is retrieved (Block 328). A difference in time is determined between the time-stamped spoken phrase and the time-stamped sensor measurement (Block 330).

The flowchart continues with FIG. 18. If the difference in time is within the window of time (Block 350), then the sensor measurement is associated with the user (Block 352). If the difference in time is outside the window of time (Block 350), then the sensor measurement cannot be bound without further information, so the sensor measurement is stored in a database, along with the associated time stamp (Block 354). The spoken phrase is compared to a database storing commands (Block 356). A command is retrieved from the database that is associated to the spoken phrase (Block 358). The command may then be executed (Block 360).

Figure 19:
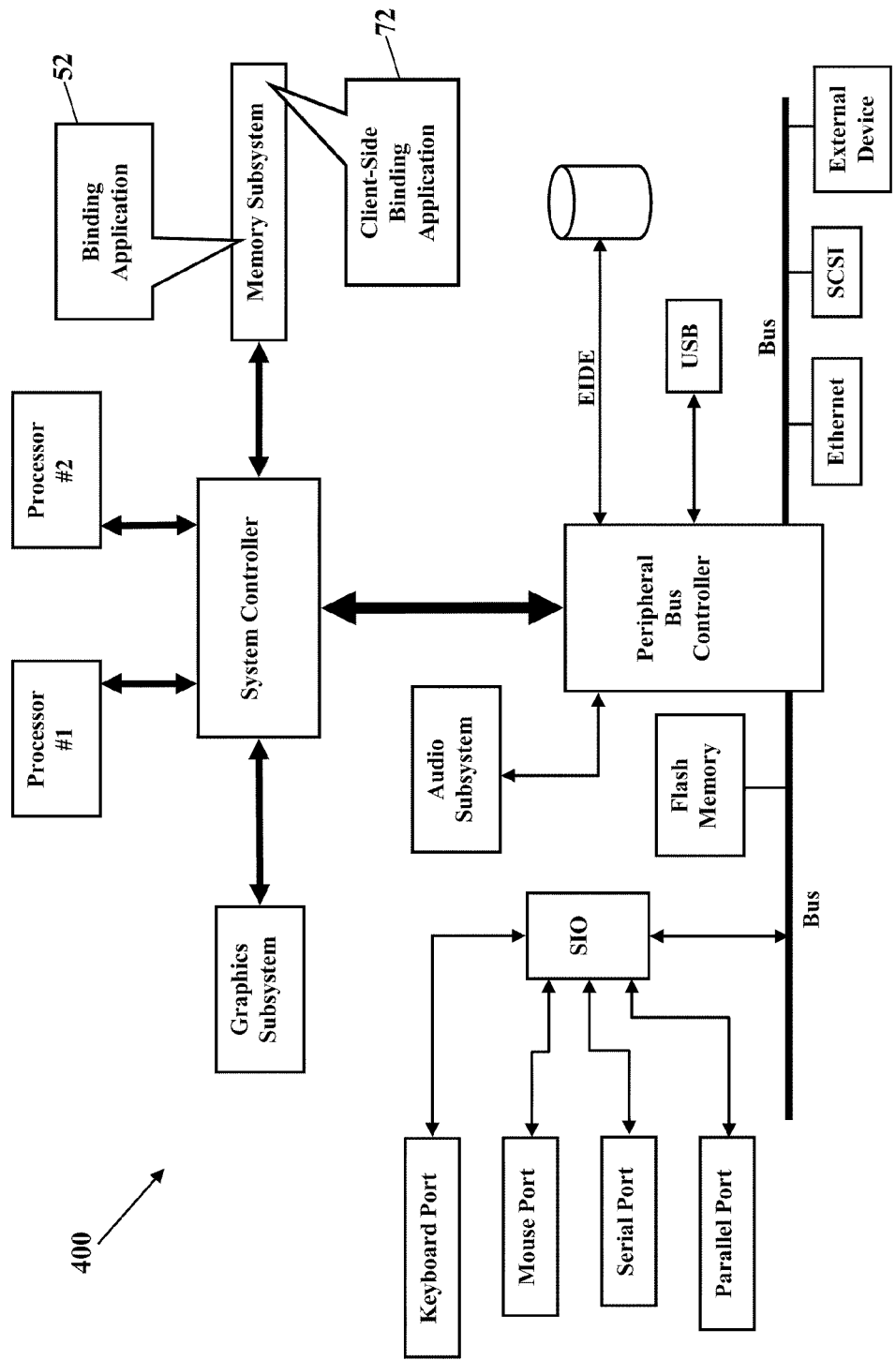
FIG. 19 is a schematic illustrating a processor-controlled device, according to exemplary embodiments.

FIG. 19 is a schematic illustrating still more exemplary embodiments. FIG. 19 is a generic block diagram illustrating the binding application 52 operating within a processor-controlled device 400. FIGS. 1-15 illustrated the binding application 52 operating within the health server 22. As paragraph [0014] explained, though, the binding application 52 may operate in any processor-controlled device 400. FIG. 19, then, illustrates the binding application 52 stored in a memory subsystem of the processor-controlled device 400. FIG. 19 also illustrates the client-side binding application 72 operating within the processor-controlled device 400. The medical measurement device 20 and the communications device 40, in other words, may be any processor-controlled device 400. One or more processors communicate with the memory subsystem and execute the binding application 52 and/or the client-side binding application 72. Because the processor-controlled device 400 is well-known to those of ordinary skill in the art, no detailed explanation is needed.

Figure 20:
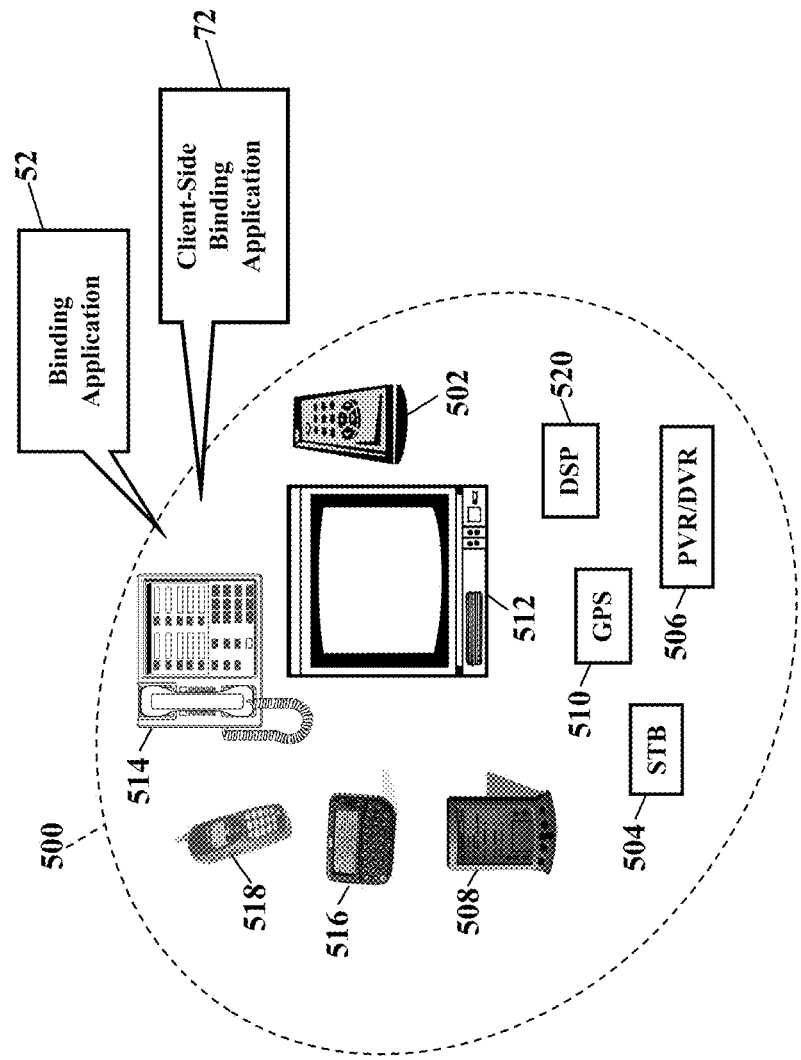
FIG. 20 depicts other possible operating environments for additional aspects of the exemplary embodiments.

FIG. 20 depicts other possible operating environments for additional aspects of the exemplary embodiments. FIG. 20 illustrates the binding application 52 and the client-side binding application 72 operating within various other devices 500. FIG. 20, for example, illustrates that the binding application 52 and/or the client-side binding application 72 may entirely or partially operate within a remote control 502, a set-top box ("STB") (504), a personal/digital video recorder (PVR/DVR) 506, a personal digital assistant (PDA) 508, a Global Positioning System (GPS) device 510, an interactive television 512, an Internet Protocol (IP) phone 514, a pager 516, a cellular/satellite phone 518, or any computer system, communications device, or processor-controlled device utilizing the processor 50 and/or a digital signal processor (DP/DSP) 520. The device 500 may also include watches, radios, vehicle electronics, clocks, printers, gateways, mobile/implantable medical devices, and other apparatuses and systems. Because the architecture and operating principles of the various devices 500 are well known, the hardware and software componentry of the various devices 500 are not further shown and described.

Figure 21:
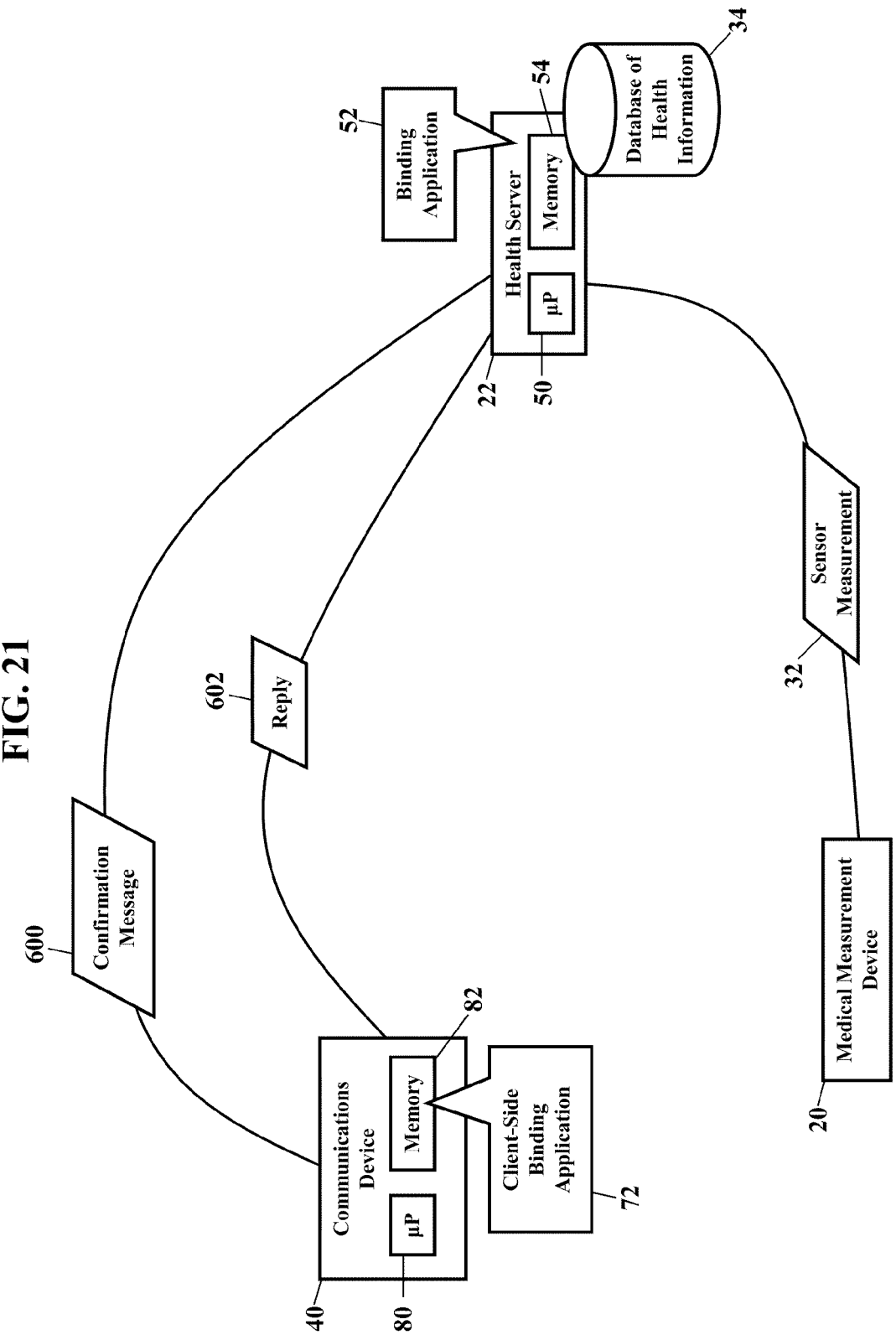
FIG. 21 is a schematic illustrating confirmation of binding, according to exemplary embodiments.

FIG. 21 is a schematic illustrating confirmation of binding, according to exemplary embodiments. As the previous paragraphs explained, the medical measurement device 20 sends the sensor measurement 32 to the health server 22. Here, though, the binding application 52 may perform a confirmation function to confirm that the binding is correct. The binding application 52 may cause the processor 50 in the health server 22 to send a confirmation message 600. The confirmation message 600 may ask or prompt the user (who provided the spoken phrase 42) to verify the sensor measurement 32. As FIG. 21 illustrates, the confirmation message 600 may be sent to a communications address associated with the communications device 40 (via the communications network 24 illustrated in FIG. 1). The confirmation message 600 may be any electronic message, such as an email, instant message, or text message. The confirmation message 600 may also be an outbound call (telephone or Voice-over Internet Protocol). The confirmation message 600 may also be a notification sent via an outbound Interactive Voice Response (IVR) system. Regardless, the confirmation message 600 instructs the user at the communications device 40 to verify the sensor measurement 32. The client-side binding application 72 causes the processor 80 (operating in the communications device 40) to send a reply 602 that confirms or denies the sensor measurement 32. If the reply 602 confirms the sensor measurement 32, then the binding application 52 associates the sensor measurement 32 to the identified user who provided the spoken phrase 42. If the reply 602 denies or rejects the sensor measurement 32, then the binding application 52 declines to associate the sensor measurement 32 to the identified user of the spoken phrase 42.

The confirmation message 600 thus helps eliminate incorrect data. If the sensor measurement 32 is grossly incorrect (compared with historical sensor measurements), then the confirmation message 600 may reduce or eliminate errant data points. Suppose, for example, that a user's historical weight readings average 165 pounds, within a ±3σ range of 5 pounds. The user's long term historical weight, in other words, has remained between 160 and 170 pounds. If the sensor measurement 32 is 210 pounds, then the confirmation message 600 would quickly determine whether the 210 pounds reading was an error. The confirmation message 600 is thus a verification that the health server 22 may use to improve the binding function. The binding application 52 may notify or call the communications device 40 for confirmation of "unusual" sensor measurements that are outside of historical norms. When an unusual sensor measurement is received, the binding application 52 may immediately email, text, call, or otherwise notify the user. The binding application 52, for example, may use a text-to-speech subsystem to audibly present a voice message "This is <ABC> healthcare provider—if you are <John Do>, please speak your name and the ZIP code of your home." Once the user is confirmed, the IVR system may say "Did you just submit a <XYZ> measurement? Please say yes or no". If the user says "Yes," the binding application 52 has confirmed that the sensor measurement 32 just received is indeed from the user.

The confirmation process may utilize any contact address. FIG. 21 illustrates the confirmation message 600 being sent to a communications address associated with the communications device 40. The confirmation message 600, however, may be sent to any contact address associated with the identified user (who provided the spoken phrase 42). The confirmation message 600 may be sent to any email address, device, Internet Protocol address, or telephone number that is on file in a profile or database.

Figure 22:
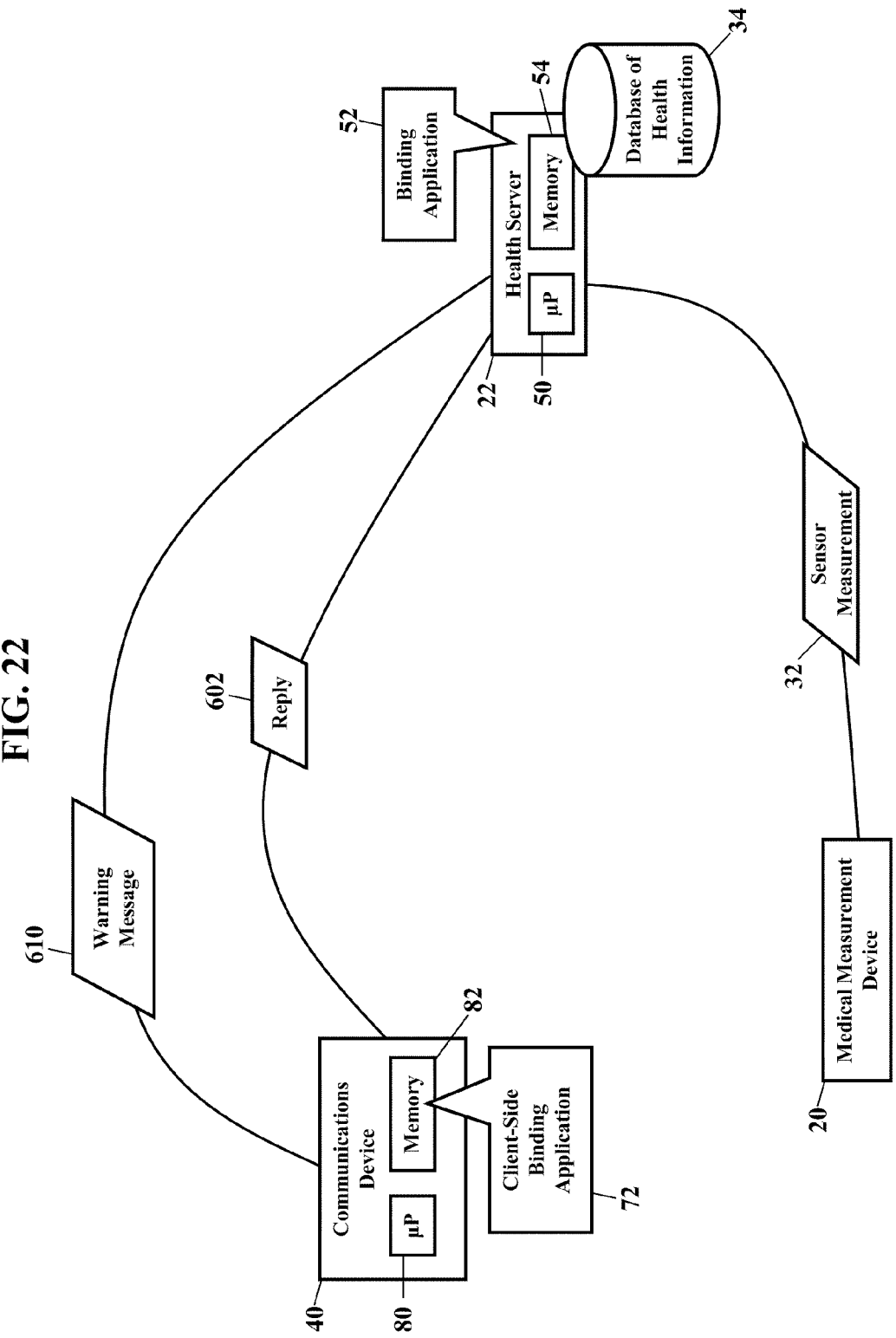
FIG. 22 is a schematic illustrating health warnings, according to exemplary embodiments.

FIG. 22 is a schematic illustrating warning messages, according to exemplary embodiments. Here the binding application 52 may warn the user of an unusual sensor measurement 32. FIG. 21 and the accompanying paragraphs explained that the confirmation message 600 helps reduce errors. Sometimes, however, the user may confirm an unusual sensor measurement 32. That is, ever though the sensor measurement 32 may be outside of historical norms, the user still sends the reply 602 that confirms the sensor measurement 32. When the reply 610 is received, the binding application 52 associates the sensor measurement 32 to the identified user, even though the sensor measurement 32 may be outside of historical norms.

The binding application 52 may then send a warning message 610. The warning message 610 visually and/or audibly warns the user that the sensor measurement 32 was outside of "normal" or historical trends. The warning message 610 may be sent to any contact address associated with the user (such as the communications address associated with the communications device 40). The warning message 610 may also be sent to physicians and family members. The warning message 610 may be any electronic message (such as an email, instant message, or text message) or outbound call (telephone or Voice-over Internet Protocol). The warning message 610 may also be a notification sent via an outbound Interactive Voice Response (IVR) system. Regardless, the warning message 610 instructs the user to immediately seek medical care.

Exemplary embodiments may be physically embodied on or in a computer-readable storage medium. This computer-readable medium may include CD-ROM, DVD, tape, cassette, floppy disk, memory card, and large-capacity disks. This computer-readable medium, or media, could be distributed to end-subscribers, licensees, and assignees. These types of computer-readable media, and other types not mention here but considered within the scope of the exemplary embodiments. A computer program product comprises processor-executable instructions for measuring a user's health, as the above paragraphs explained.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

What is claimed is:

1. A method of measuring health, comprising:
  receiving, at a server, a time-stamped spoken phrase sent from a mobile communications device;
  identifying a user from the time-stamped spoken phrase;
  voice recognizing a window of time from a semantic content of the time-stamped spoken phrase;

receiving a time-stamped physiological sensor measurement sent from a medical measurement device to the server;

determining by the server a difference in time between the time-stamped spoken phrase received from the mobile communications device and the time-stamped physiological sensor measurement received from the medical measurement device;

comparing, by the server, the difference in time to the window of time determined from the semantic content of the time-stamped spoken phrase; and when the difference in time is within the window of time, binding the physiological sensor measurement to the user from among a group of users in a database.

2. The method according to claim 1, further comprising comparing the time-stamped spoken phrase to entries in a database of commands storing commands.

3. The method according to claim 2, further comprising retrieving a command from the database of commands that is associated to the time-stamped spoken phrase.

4. The method according to claim 1, further comprising receiving a device identifier associated with a device that recorded the time-stamped spoken phrase.

5. The method according to claim 4, wherein the device identifier is selected from a telephone number and an Internet Protocol address.

6. The method according to claim 4, further comprising querying another database for the device identifier.

7. The method according to claim 6, further comprising retrieving a subgroup of the group of users, the subgroup being associated with the device identifier.

8. The method according to claim 1, further comprising receiving a sensor identifier associated with a sensor that measured the physiological measurement.

9. The method according to claim 8, further comprising querying another database for the sensor identifier.

10. The method according to claim 9, further comprising retrieving a subgroup of the group of users, the subgroup being associated with the sensor identifier.

11. A system, comprising:
a processor; and
memory for storing code that when executed causes the processor to perform operations, the operations comprising:
receiving a time-stamped spoken phrase from a mobile communications device;
identifying a user from the time-stamped spoken phrase;
voice recognizing a window of time from a semantic content of the time-stamped spoken phrase;
receiving a time-stamped physiological measurement from a medical measurement device;
determining a difference in time between the time-stamped spoken phrase received from the mobile communications device and the time-stamped sensor measurement received from the medical measurement device;
comparing, by the server, the difference in time to the window of time determined from the semantic content of the time-stamped spoken phrase; and
when the difference in time is within the window of time, then binding the physiological measurement to the user from among a group of users in a database that is stored in the memory.

12. The system according to claim 11, wherein the operations further comprise:
comparing the time-stamped spoken phrase to a database of commands that stores commands; and
retrieving a command from the database of commands associated with the time-stamped spoken phrase.

13. The system according to claim 11, wherein the operations further comprise:
receiving a device identifier associated with a device that recorded the time-stamped spoken phrase;
querying the database for a subset of the group of users, the subset being associated with the device identifier; and
reducing a pool of candidates to the subset of the group of users who are associated with the device identifier.

14. The system according to claim 13, wherein the operations further comprise selecting the device identifier from a telephone number and an Internet Protocol address.

15. The system according to claim 13, wherein the operations further comprise receiving a sensor identifier associated with a sensor that measured the physiological measurement.

16. The system according to claim 15, wherein the operations further comprise:
querying for the sensor identifier;
retrieving a subgroup of the group of users, the subgroup being associated with the sensor identifier; and
reducing a pool of candidates to the subgroup who are associated with the sensor identifier.

17. A computer readable memory storing processor executable instructions that when executed by a processor cause the processor to perform operations at a server, the operations comprising:
receiving a time-stamped spoken phrase sent from a mobile communications device;
identifying a user from the time-stamped spoken phrase;
voice recognizing a window of time from a semantic content of the time-stamped spoken phrase;
receiving a time-stamped physiological sensor measurement from a medical measurement device;
determining a difference in time between the time-stamped spoken phrase received from the mobile communications device and the time-stamped physiological sensor measurement received from the medical measurement device;
comparing the difference in time to the window of time determined from the semantic content of the time-stamped spoken phrase; and
when the difference in time is within the window of time, then binding the physiological sensor measurement to the user selected from among a group of users in a database.

18. The computer readable memory according to claim 17, wherein the operations further comprise:
comparing the time-stamped spoken phrase to a database of commands storing commands; and
retrieving a command from the database of commands that is associated to the time-stamped spoken phrase.

19. The computer readable memory according to claim 17, wherein the operations further comprise determining a command from the semantic content of the time-stamped spoken phrase.

20. The computer readable memory according to claim 17, wherein the operations further comprise:
receiving a device identifier associated with a device that recorded the time-stamped spoken phrase;
querying for a subgroup of the group of users, the subgroup being associated with the device identifier; and
reducing a pool of candidates to the subgroup who are associated with the device identifier.

* * * * *